US010196458B2

(12) United States Patent
Zhang et al.

(10) Patent No.: US 10,196,458 B2
(45) Date of Patent: Feb. 5, 2019

(54) ANTI-IMMUNOGLOBULIN E ANTIBODIES AND METHODS OF USING THEREOF

(71) Applicants:The Regents of the University of California, Oakland, CA (US); Sixal, Inc., Santa Monica, CA (US)

(72) Inventors: Ke Zhang, Los Angeles, CA (US); Andrew Saxon, Santa Monica, CA (US)

(73) Assignees: The Regents of the University of California, Oakland, CA (US); Sixal, Inc., Santa Monica, CA (US)

( * ) Notice: Subject to any disclaimer, the term of this patent is extended or adjusted under 35 U.S.C. 154(b) by 0 days.

(21) Appl. No.: 14/906,026

(22) PCT Filed: Jul. 25, 2014

(86) PCT No.: PCT/US2014/048284
§ 371 (c)(1),
(2) Date: Jan. 19, 2016

(87) PCT Pub. No.: WO2015/013668
PCT Pub. Date: Jan. 29, 2015

(65) Prior Publication Data
US 2016/0168268 A1      Jun. 16, 2016

Related U.S. Application Data

(60) Provisional application No. 61/859,055, filed on Jul. 26, 2013.

(51) Int. Cl.
*A61K 39/395*   (2006.01)
*C07K 16/42*    (2006.01)
*A61K 39/00*    (2006.01)

(52) U.S. Cl.
CPC .... *C07K 16/4291* (2013.01); *A61K 2039/505* (2013.01); *C07K 2317/24* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 5,543,144 A | | 8/1996 | Chang | |
| 5,693,762 A | * | 12/1997 | Queen | C07K 16/00 424/133.1 |
| 5,958,708 A | * | 9/1999 | Hardman | C07K 16/4291 435/7.21 |
| 5,994,511 A | * | 11/1999 | Lowman | C07K 16/00 424/133.1 |
| 7,157,085 B2 | * | 1/2007 | Lowman | A61K 39/39566 424/133.1 |
| 2006/0234296 A1 | * | 10/2006 | Singh | C07K 16/4291 435/7.1 |

FOREIGN PATENT DOCUMENTS

| | | | | |
|---|---|---|---|---|
| CA | 2441048 | | 12/2011 | |
| EP | 1857116 | | 11/2007 | |
| EP | 2407485 | | 1/2012 | |
| WO | WO 8906138 A1 | * | 7/1989 | ........... A61K 39/395 |
| WO | WO 9111456 A1 | * | 8/1991 | ....... A61K 47/48284 |
| WO | WO 9217207 A1 | * | 10/1992 | ....... A61K 47/48653 |
| WO | WO 0041722 A1 | * | 7/2000 | ............. C07K 16/28 |
| WO | WO 2008103905 A2 | * | 8/2008 | ....... C07K 14/70535 |
| WO | 2008/133722 A2 | | 11/2008 | |

OTHER PUBLICATIONS

Belliveau, Paul P., MedGenMed. Jan. 27, 2005;7(1):27.*
Shiung et al., Immunobiology. Jul. 2012;217(7):676-83. doi: 10.1016/j.imbio.2011.11.006. Epub Nov. 25, 2011.*
Haak-Frendscho et al., Immunology. Jun. 1994;82(2):306-13.*
Characteristics sheet for CIA-E-7.12 downloaded Jul. 5, 2017 from www.atcc.org, one page.*
Scandella et al., Blood. Oct. 1989;74(5):1618-26.*
Rudikoff et al., Proc Natl Acad Sci U S A. Mar. 1982;79(6):1979-83.*
Janeway et al., Immunobiology, 3rd edition, 1997, Garland Publications, Inc., pp. 3:1-3:11.*
Poosarla et al., Biotechnol Bioeng. Jun. 2017;114(6):1331-1342. doi: 10.1002/bit.26244. Epub Feb. 2, 2017.*
Edwards et al., J Mol Biol. Nov. 14, 2003;334(1):103-18.*
Antibody Affinity and Affinity Maturation, downloaded Sep. 14, 2018 from https://www.pacificimmunology.com/resources/antibody-introduction/antibody-affinity-and-affinity-maturation/.*
International Search Report received in PCT/US2014/048284, dated Dec. 5, 2014.
Written Opinion received in PCT/US2014/048284, dated Dec. 5, 2014.

* cited by examiner

*Primary Examiner* — Michael Szperka
(74) *Attorney, Agent, or Firm* — Suzannah K. Sundby, Esq.; Canady + Lortz LLP

(57) ABSTRACT

The present disclosure provides antibodies that specifically bind to circulating and receptor-bound IgE and inhibit IgE-mediated cell activation. The antibodies find use in various treatment, diagnostic, and monitoring applications, which are also provided.

15 Claims, 14 Drawing Sheets
Specification includes a Sequence Listing.

FIG. 1

P6.2 VH DNA sequence

CAGGTCCAGCTGCAGCAGTCTGGAGCTGAGCTGGTAAGGCCTGGGGCTTCAGTGAAGATACCC
TCACTAATTACTTGATAGTAGAAGCAGAGGCCTGGAGTGGATTGGAGTGATTAATCCTGGAAGTGGT
TTTACAAATACAAGTCGAAGTTCAACGGCAAGGCCACACTGACTGTAGACAAATCCTCCAGCACC
AGCGCTACATCCATCTGGAACTCTGCAGTCTGAGGACTCTGCAGTCTATTACTGTGCAAGAGAAGAT
GTGTACTCTTGGCCTGCTTACTGGGGCCAAGGGACTCTGGTCACTGTCTCTGCA

P6.2 VH Protein sequence

Q V Q L Q Q S G A E L V R P G T S V K V S C K A S G Y A F T N Y L I E W V K Q
                                                        CDR1
R P G Q G L E W I G V I N P G S G F T N Y N E K F K G K A T L T A D K S S S T
                        CDR2
A Y M H L S S L T S D D S A V Y F C A R E D V Y S W P A Y W G Q G T L V T V S
                                        CDR3
A

P6.2 VL DNA sequence

GACATTGTGCTGACCCAATCTCCAGCTTCTTTGGCTGTGTCTCTAGGGCAGAGGGCCACCATCTCC
TGCAGAGCCAGTGAAAGTGTTGATAGTTATGGCAATAGTTTTATGCACTGGTACCAGCAGAAACCA
GGACAGCCACCCAAACTCCTCATCTATCGTACATCC
AACCTAGAATCTGGGATCCCTGCCAGGTTCAGTGGCAGTGGGTCAGGGACAGACTTCACCCTCACC
ATTAATCCTGTGGAGGCTGATGATGTTGCAACCTATTACTGTCAGCAAAGTTATGAGGATCCGTTC
TTCTTCGGCTCTGGGACAAAGTTGGAAATAAAA

P6.2 VL protein sequence

D I V L T Q S P A S L A V S L G Q R A T I S C R A S E S V D S Y G N S F M H W Y Q Q
                                                    CDR1
K P G Q P P K L L I Y R T S N L E S G I P A R F S G S G S R T D F T L T I N P V E A
                    CDR2
D D V A T Y Y C Q Q S Y E D P F F F G S G T K L E I K
                        CDR3

FIG. 12 (Cont'd)
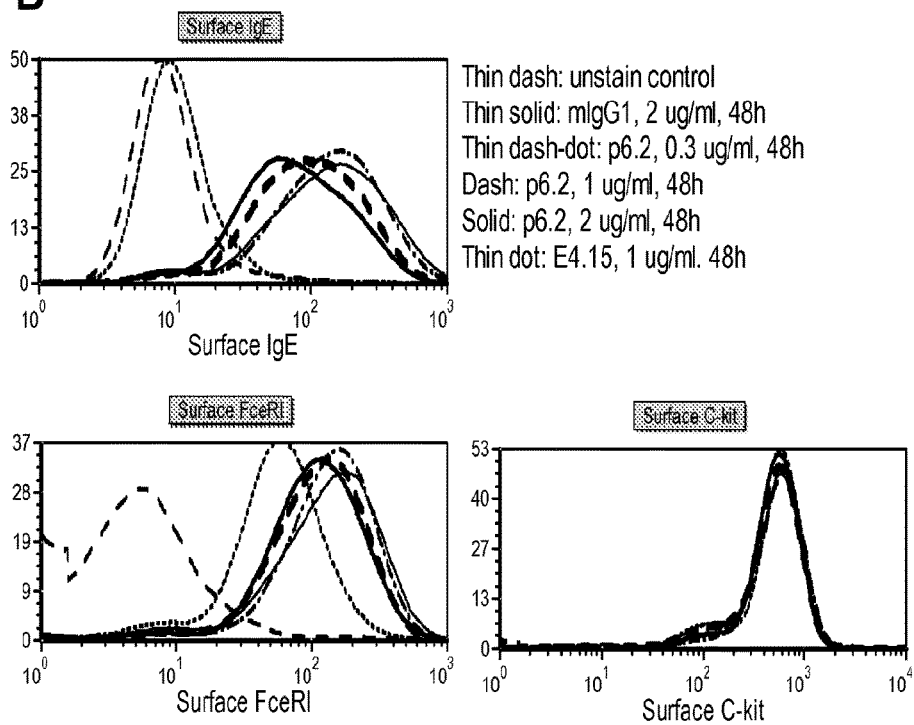
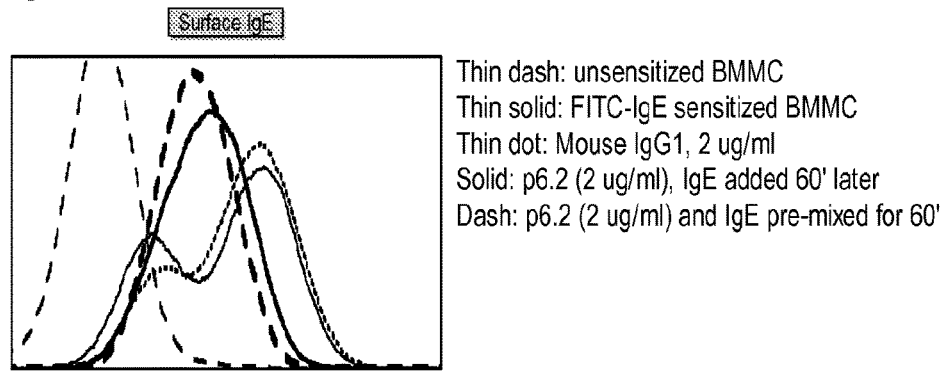

SEQUENCE LISTING

```
<160> NUMBER OF SEQ ID NOS: 29

<210> SEQ ID NO 1
<211> LENGTH: 5
<212> TYPE: PRT
<213> ORGANISM: Artificial Sequence
<220> FEATURE:
<223> OTHER INFORMATION: synthetic polypeptide sequence

<400> SEQUENCE: 1

Asn Tyr Leu Ile Glu
1               5

<210> SEQ ID NO 2
<211> LENGTH: 17
<212> TYPE: PRT
<213> ORGANISM: Artificial Sequence
<220> FEATURE:
<223> OTHER INFORMATION: synthetic polypeptide sequence

<400> SEQUENCE: 2

Val Ile Asn Pro Gly Ser Gly Phe Thr Lys Tyr Asn Glu Lys Phe Lys
1               5                   10                  15

Gly

<210> SEQ ID NO 3
<211> LENGTH: 20
<212> TYPE: PRT
<213> ORGANISM: Artifical sequence
<220> FEATURE:
<223> OTHER INFORMATION: synthetic polypeptide sequence

<400> SEQUENCE: 3

Glu Asp Val Tyr Ser Trp Phe Ala Tyr Trp Gly Gln Gly Thr Leu Val
1               5                   10                  15

Thr Val Ser Ala
            20

<210> SEQ ID NO 4
<211> LENGTH: 15
<212> TYPE: PRT
<213> ORGANISM: Artifical sequence
<220> FEATURE:
<223> OTHER INFORMATION: synthetic polypeptide sequence
```

<400> SEQUENCE: 4

Arg Ala Ser Glu Ser Val Asp Ser Tyr Gly Asn Ser Phe Met His
1               5                   10                  15

<210> SEQ ID NO 5
<211> LENGTH: 7
<212> TYPE: PRT
<213> ORGANISM: Artifical sequence
<220> FEATURE:
<223> OTHER INFORMATION: synthetic polypeptide sequence

<400> SEQUENCE: 5

Arg Thr Ser Asn Leu Glu Ser
1               5

<210> SEQ ID NO 6
<211> LENGTH: 19
<212> TYPE: PRT
<213> ORGANISM: Artifical sequence
<220> FEATURE:
<223> OTHER INFORMATION: synthetic polypeptide sequence

<400> SEQUENCE: 6

Gln Gln Ser Tyr Glu Asp Pro Phe Thr Phe Gly Ser Gly Thr Lys Leu
1               5                   10                  15

Glu Ile Lys

<210> SEQ ID NO 7
<211> LENGTH: 118
<212> TYPE: PRT
<213> ORGANISM: Mus musculus

<400> SEQUENCE: 7

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
                20                  25                  30

Leu Ile Glu Trp Val Lys Gln Arg Pro Gly Gln Gly Leu Glu Trp Ile
            35                  40                  45

Gly Val Ile Asn Pro Gly Ser Gly Phe Thr Lys Tyr Asn Glu Lys Phe
        50                  55                  60

Lys Gly Lys Ala Thr Leu Thr Ala Asp Lys Ser Ser Ser Thr Ala Tyr
65                  70                  75                  80

Met His Leu Ser Ser Leu Thr Ser Asp Asp Ser Ala Val Tyr Phe Cys
                85                  90                  95

Ala Arg Glu Asp Val Tyr Ser Trp Phe Ala Tyr Trp Gly Gln Gly Thr
                100                 105                 110

Leu Val Thr Val Ser Ala
            115

<210> SEQ ID NO 8
<211> LENGTH: 111
<212> TYPE: PRT
<213> ORGANISM: Mus musculus

<400> SEQUENCE: 8

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
                20                  25                  30

```
Gly Asn Ser Phe Met His Trp Tyr Gln Gln Lys Pro Gly Gln Pro
             35                  40                  45

Lys Leu Leu Ile Tyr Arg Thr Ser Asn Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Phe Cys Gln Gln Ser Tyr
                 85                  90                  95

Glu Asp Pro Phe Thr Phe Gly Ser Gly Thr Lys Leu Glu Ile Lys
            100                 105                 110
```

<210> SEQ ID NO 9
<211> LENGTH: 354
<212> TYPE: DNA
<213> ORGANISM: Mus musculus

<400> SEQUENCE: 9

```
caggtccagc tgcagcagtc tggagctgag ctggtaaggc ctgggacttc agtgaaggtg      60
tcctgcaagg cttctggata cgccttcact aattacttga tagagtgggt aaagcagagg     120
cctggacagg gccttgagtg gattggagtg attaatcctg aagtggtttt acaaaaatac     180
aatgagaagt tcaagggcaa ggcaacactg actgcagaca atcctccag cactgcctac      240
atgcacctca gcagcctgac atctgatgac tctgcggtct attctgtgc aagagaagat      300
gtttactcct ggtttgctta ctggggccaa gggactctgg tcactgtctc tgca           354
```

<210> SEQ ID NO 10
<211> LENGTH: 333
<212> TYPE: DNA
<213> ORGANISM: Mus musculus

<400> SEQUENCE: 10

```
gacattgtgc tgacccaatc tccagcttct ttggctgtgt ctctagggca gagggccacc      60
atatcctgca gagccagtga agtgttgat agttatggca atagtttat gcactggtac       120
cagcagaaac aggacagcc acccaaactc ctcatctatc gtacatccaa cctagaatct      180
gggatccctg ccaggttcag tggcagtggg tctaggacag acttcaccct caccattaat     240
cctgtggagg ctgatgatgt tgcaacctat ttctgtcagc aaagttatga ggatccattc    300
acgttcggct cggggacaaa gttggaaata aaa                                  333
```

<210> SEQ ID NO 11
<211> LENGTH: 10
<212> TYPE: PRT
<213> ORGANISM: Artificial sequence
<220> FEATURE:
<223> OTHER INFORMATION: synthetic polypeptide sequence

<400> SEQUENCE: 11

```
Cys Tyr Pro Tyr Asp Val Pro Asp Tyr Ala
 1               5                  10
```

<210> SEQ ID NO 12
<211> LENGTH: 8
<212> TYPE: PRT
<213> ORGANISM: Artificial sequence
<220> FEATURE:
<223> OTHER INFORMATION: synthetic polypeptide sequence

<400> SEQUENCE: 12

```
Asp Tyr Lys Asp Asp Asp Asp Lys
1               5

<210> SEQ ID NO 13
<211> LENGTH: 11
<212> TYPE: PRT
<213> ORGANISM: Artifical sequence
<220> FEATURE:
<223> OTHER INFORMATION: synthetic polypeptide sequence

<400> SEQUENCE: 13

Cys Glu Gln Lys Leu Ile Ser Glu Glu Asp Leu
1               5                   10

<210> SEQ ID NO 14
<211> LENGTH: 5
<212> TYPE: PRT
<213> ORGANISM: Artifical sequence
<220> FEATURE:
<223> OTHER INFORMATION: synthetic polypeptide sequence

<400> SEQUENCE: 14

His His His His His
1               5

<210> SEQ ID NO 15
<211> LENGTH: 6
<212> TYPE: PRT
<213> ORGANISM: Artifical sequence
<220> FEATURE:
<223> OTHER INFORMATION: synthetic polypeptide sequence

<400> SEQUENCE: 15

His His His His His His
1               5

<210> SEQ ID NO 16
<211> LENGTH: 10
<212> TYPE: PRT
<213> ORGANISM: Artifical sequence
<220> FEATURE:
<223> OTHER INFORMATION: synthetic polypeptide sequence

<400> SEQUENCE: 16

Glu Gln Lys Leu Ile Ser Glu Glu Asp Leu
1               5                   10

<210> SEQ ID NO 17
<211> LENGTH: 8
<212> TYPE: PRT
<213> ORGANISM: Artifical sequence
<220> FEATURE:
<223> OTHER INFORMATION: synthetic polypeptide sequence

<400> SEQUENCE: 17

Trp Ser His Pro Gln Phe Glu Lys
1               5

<210> SEQ ID NO 18
<211> LENGTH: 9
<212> TYPE: PRT
<213> ORGANISM: Artifical sequence
<220> FEATURE:
<223> OTHER INFORMATION: synthetic polypeptide sequence

<400> SEQUENCE: 18

Tyr Pro Tyr Asp Val Pro Asp Tyr Ala
```

```
1               5
```

<210> SEQ ID NO 19
<211> LENGTH: 5
<212> TYPE: PRT
<213> ORGANISM: Artifical sequence
<220> FEATURE:
<223> OTHER INFORMATION: synthetic polypeptide sequence

<400> SEQUENCE: 19

```
Arg Tyr Ile Arg Ser
1               5
```

<210> SEQ ID NO 20
<211> LENGTH: 4
<212> TYPE: PRT
<213> ORGANISM: Artifical sequence
<220> FEATURE:
<223> OTHER INFORMATION: synthetic polypeptide sequence

<400> SEQUENCE: 20

```
Phe His His Thr
1
```

<210> SEQ ID NO 21
<211> LENGTH: 17
<212> TYPE: PRT
<213> ORGANISM: Artifical sequence
<220> FEATURE:
<223> OTHER INFORMATION: synthetic polypeptide sequence

<400> SEQUENCE: 21

```
Trp Glu Ala Ala Ala Arg Glu Ala Cys Cys Arg Glu Cys Cys Ala Arg
1               5                   10                  15

Ala
```

<210> SEQ ID NO 22
<211> LENGTH: 5
<212> TYPE: PRT
<213> ORGANISM: Artifical sequence
<220> FEATURE:
<223> OTHER INFORMATION: synthetic polypeptide sequence

<400> SEQUENCE: 22

```
Gly Ser Gly Gly Ser
1               5
```

<210> SEQ ID NO 23
<211> LENGTH: 4
<212> TYPE: PRT
<213> ORGANISM: Artifical sequence
<220> FEATURE:
<223> OTHER INFORMATION: synthetic polypeptide sequence

<400> SEQUENCE: 23

```
Gly Gly Gly Ser
1
```

<210> SEQ ID NO 24
<211> LENGTH: 4
<212> TYPE: PRT
<213> ORGANISM: Artifical sequence
<220> FEATURE:
<223> OTHER INFORMATION: synthetic polypeptide sequence

<400> SEQUENCE: 24

Gly Gly Ser Gly
1

<210> SEQ ID NO 25
<211> LENGTH: 5
<212> TYPE: PRT
<213> ORGANISM: Artifical sequence
<220> FEATURE:
<223> OTHER INFORMATION: synthetic polypeptide sequence

<400> SEQUENCE: 25

Gly Gly Ser Gly Gly
1               5

<210> SEQ ID NO 26
<211> LENGTH: 5
<212> TYPE: PRT
<213> ORGANISM: Artifical sequence
<220> FEATURE:
<223> OTHER INFORMATION: synthetic polypeptide sequence

<400> SEQUENCE: 26

Gly Ser Gly Ser Gly
1               5

<210> SEQ ID NO 27
<211> LENGTH: 5
<212> TYPE: PRT
<213> ORGANISM: Artifical sequence
<220> FEATURE:
<223> OTHER INFORMATION: synthetic polypeptide sequence

<400> SEQUENCE: 27

Gly Ser Gly Gly Gly
1               5

<210> SEQ ID NO 28
<211> LENGTH: 5
<212> TYPE: PRT
<213> ORGANISM: Artifical sequence
<220> FEATURE:
<223> OTHER INFORMATION: synthetic polypeptide sequence

<400> SEQUENCE: 28

Gly Gly Gly Ser Gly
1               5

<210> SEQ ID NO 29
<211> LENGTH: 5
<212> TYPE: PRT
<213> ORGANISM: Artifical sequence
<220> FEATURE:
<223> OTHER INFORMATION: synthetic polypeptide sequence

<400> SEQUENCE: 29

Gly Ser Ser Ser Gly
1               5

ANTI-IMMUNOGLOBULIN E ANTIBODIES AND METHODS OF USING THEREOF

CROSS-REFERENCE TO RELATED APPLICATIONS

This application claims priority benefit to U.S. provisional application Ser. No. 61/859,055 filed on Jul. 26, 2013, which application is incorporated herein by reference in its entirety.

STATEMENT REGARDING FEDERALLY SPONSORED RESEARCH

This invention was made with Government support under AI102279, awarded by the National Institutes of Health. The government has certain rights in the invention.

REFERENCE TO A SEQUENCE LISTING SUBMITTED VIA EFS-WEB

The content of the ASCII text file of the sequence listing named "*_seq" which is 8.25 kb in size has a created date of Jan. 19, 2016 (and a modified date of Sep. 26, 2014 as a result of an electronic file transfer to a new agent) and electronically submitted via EFS-Web herewith the application papers is incorporated herein by reference in its entirety.

INTRODUCTION

Immunoglobulin E (IgE) constitutes one of the five major classes of antibodies in humans. IgE is a single four-chain unit consisting of two ε heavy chains and two κ light chains or two λ light chains. IgE is synthesized and secreted by B cells that have undergone heavy-chain class switching from μ to ε heavy chain production. Although IgE represents less than one percent of total Ig in blood, this immunoglobulin is a central player in the allergic response.

The immediate allergic response, immediate hypersensitivity or the type I allergic response, is mediated by a complex that includes IgE and FcεRI (the high-affinity receptor for IgE). This complex is formed upon binding of the Fc region of secreted IgE antibodies to FcεRI receptors on the surface of effector cells such as mast cells and basophils. The bound IgE antibodies then serve as effector cell-surface receptors for those antigens, termed allergens, that trigger a type I allergic response. When antigen (e.g., allergen) binds to FcεRI-bound IgE so as to cross-link neighboring IgE/FcεRI complexes, it signals the effector cell to release histamine and other biologically active mediators by exocytosis.

SUMMARY

The present disclosure provides antibodies that specifically bind to circulating and receptor-bound IgE and inhibit IgE-mediated cell activation. The antibodies find use in various treatment, diagnostic, and monitoring applications, which are also provided.

In certain aspects, the present disclosure provides methods of treating an IgE-mediated disorder. According to certain embodiments, the methods include administering to a patient in need thereof a therapeutically effective amount of an anti-IgE antibody or IgE binding fragment thereof that: specifically binds to circulating and receptor-bound IgE; binds to IgE with low affinity (e.g., an affinity of from $1 \times 10^{-5}$ M to $1 \times 10^{-9}$ M Kd); and inhibits activation of cells that express the high affinity IgE receptor (FcεRI). Cells that express FcεRI include basophils, mast cells, eosinophils, and the like.

According to certain embodiments, the methods of treating an IgE-mediated disorder include administering to a patient in need thereof a therapeutically effective amount of an anti-IgE antibody or IgE binding fragment thereof that: specifically binds to circulating and receptor-bound IgE; does not compete for IgE binding with the antibody CIA-E-7.12 (ATCC Accession No. HB-236); and inhibits activation of cells that express the high affinity IgE receptor (FcεRI). Cells that express FcεRI include basophils, mast cells, eosinophils, and the like.

In certain aspects, an anti-IgE antibody or IgE binding fragment thereof of the present disclosure competes for specific binding to IgE with an antibody or fragment thereof that includes: a heavy chain complementary determining region 1 (HCDR1) having the amino acid sequence of SEQ ID NO:1; a heavy chain complementary determining region 2 (HCDR2) having the amino acid sequence of SEQ ID NO:2; a heavy chain complementary determining region 3 (HCDR3) having the amino acid sequence of SEQ ID NO:3; a light chain complementary determining region 1 (LCDR1) having the amino acid sequence of SEQ ID NO:4; a light chain complementary determining region 2 (LCDR2) having the amino acid sequence of SEQ ID NO:5; and a light chain complementary determining region 3 (LCDR3) having the amino acid sequence of SEQ ID NO:6.

According to certain embodiments, an anti-IgE antibody or IgE binding fragment thereof of the present disclosure includes: a heavy chain complementary determining region 1 (HCDR1) having the amino acid sequence of SEQ ID NO:1; a heavy chain complementary determining region 2 (HCDR2) having the amino acid sequence of SEQ ID NO:2; a heavy chain complementary determining region 3 (HCDR3) having the amino acid sequence of SEQ ID NO:3; a light chain complementary determining region 1 (LCDR1) having the amino acid sequence of SEQ ID NO:4; a light chain complementary determining region 2 (LCDR2) having the amino acid sequence of SEQ ID NO:5; and a light chain complementary determining region 3 (LCDR3) having the amino acid sequence of SEQ ID NO:6.

In certain aspects, the anti-IgE antibody or IgE binding fragment thereof includes a heavy chain polypeptide including a variable region having an amino acid sequence that is 85% or more identical to the heavy chain variable region set forth in SEQ ID NO:7. According to certain embodiments, the anti-IgE antibody or IgE binding fragment thereof includes a light chain polypeptide including a variable region having an amino acid sequence that is 85% or more identical to the light chain variable region set forth in SEQ ID NO:8. In still other aspects, the anti-IgE antibody or IgE binding fragment thereof includes: a heavy chain polypeptide including a variable region having an amino acid sequence that is 85% or more identical to the heavy chain variable region set forth in SEQ ID NO:7, and a light chain polypeptide including a variable region having an amino acid sequence that is 85% or more identical to the light chain variable region set forth in SEQ ID NO:8.

According to certain embodiments, the antibody is an anti-IgE antibody or IgE binding fragment thereof selected from an IgG, Fv, scFv, Fab, F(ab')2, or Fab'. In certain aspects, the anti-IgE antibody or IgE binding fragment thereof is a bivalent antibody or fragment thereof (e.g., an antibody having two heavy chain polypeptides and two light chain polypeptides, or fragments thereof). In other aspects, the anti-IgE antibody or IgE binding fragment thereof is an anti-IgE half antibody. An anti-IgE half antibody may include one or more amino acid substitutions in the hinge region of the half antibody which prevent heavy chain dimerization. The one or more amino acid substitutions may be one or more cysteine substitutions, e.g., one or more cysteine to serine substitutions.

In certain aspects, the antibody employed in the methods of the present disclosure reduces the amount of IgE bound to the surface of cells that express the high affinity IgE receptor (FcεRI) (e.g., basophils, mast cells, eosinophils, and/or the like), e.g., by triggering internalization of surface-bound IgE by the cells (e.g., internalization of IgE-FcεRI complexes on the surface of the cells).

According to certain embodiments, the anti-IgE antibody or IgE binding fragment thereof employed in the methods reduces the amount of high affinity IgE receptor (FcεRI) on the surface of cells (e.g., basophils, mast cells, eosinophils, and/or the like), e.g., by triggering internalization of FcεRIs by the cells (e.g., internalization of IgE-FcεRI complexes on the surface of the cells).

In certain aspects, the antibody employed in the methods of the present disclosure activates piecemeal degranulation in the cells (e.g., basophils, mast cells, eosinophils, and/or the like).

According to certain embodiments, the anti-IgE antibody or IgE binding fragment thereof employed in the methods binds to membrane IgE (mIgE).

Any anti-IgE antibody or IgE binding fragment thereof of the present disclosure may be a monoclonal anti-IgE antibody or IgE binding fragment thereof. In certain aspects, the anti-IgE antibody or IgE binding fragment thereof of the present disclosure is a humanized monoclonal anti-IgE antibody or IgE binding fragment thereof.

The methods of the present disclosure find use in treating a variety of IgE-mediated disorders, including asthma, allergic rhinitis, atopic dermatitis, urticaria, angioedema, and anaphylactic hypersensitivity.

Also provided by the present disclosure are pharmaceutical compositions. The compositions may include an anti-IgE antibody or IgE binding fragment thereof according to any of the embodiments described elsewhere herein. For example, in certain aspects, the composition includes an antibody or IgE binding fragment thereof that specifically binds to circulating and receptor-bound IgE; binds to IgE with low affinity (e.g., an affinity of from $1\times10^{-5}$M to $1\times10^{-9}$M Kd); and inhibits activation of cells that express the high affinity IgE receptor (FcεRI). According to certain embodiments, the composition includes an antibody or IgE binding fragment thereof that specifically binds to circulating and receptor-bound IgE; does not compete for IgE binding with the antibody CIA-E-7.12 (ATCC Accession No. HB-236); and inhibits activation of cells that express the high affinity IgE receptor (FcεRI). The pharmaceutical compositions of the present disclosure include a pharmaceutically acceptable carrier as described in further detail below.

BRIEF DESCRIPTION OF THE DRAWINGS

FIG. 1 provides amino acid sequences of the heavy chain variable ($V_H$) and light chain variable ($V_L$) regions of an example anti-IgE antibody (antibody P6.2) according to one embodiment of the present disclosure. Complementarity determining regions (CDRs) are underlined. Also provided are the nucleic acid sequences that encode the $V_H$ and $V_L$ regions. The SEQ ID NOs of the sequences from top to bottom are SEQ ID NO:9, SEQ ID NO:7, SEQ ID NO:10, and SEQ ID NO:8.

DEFINITIONS

Figure 2:
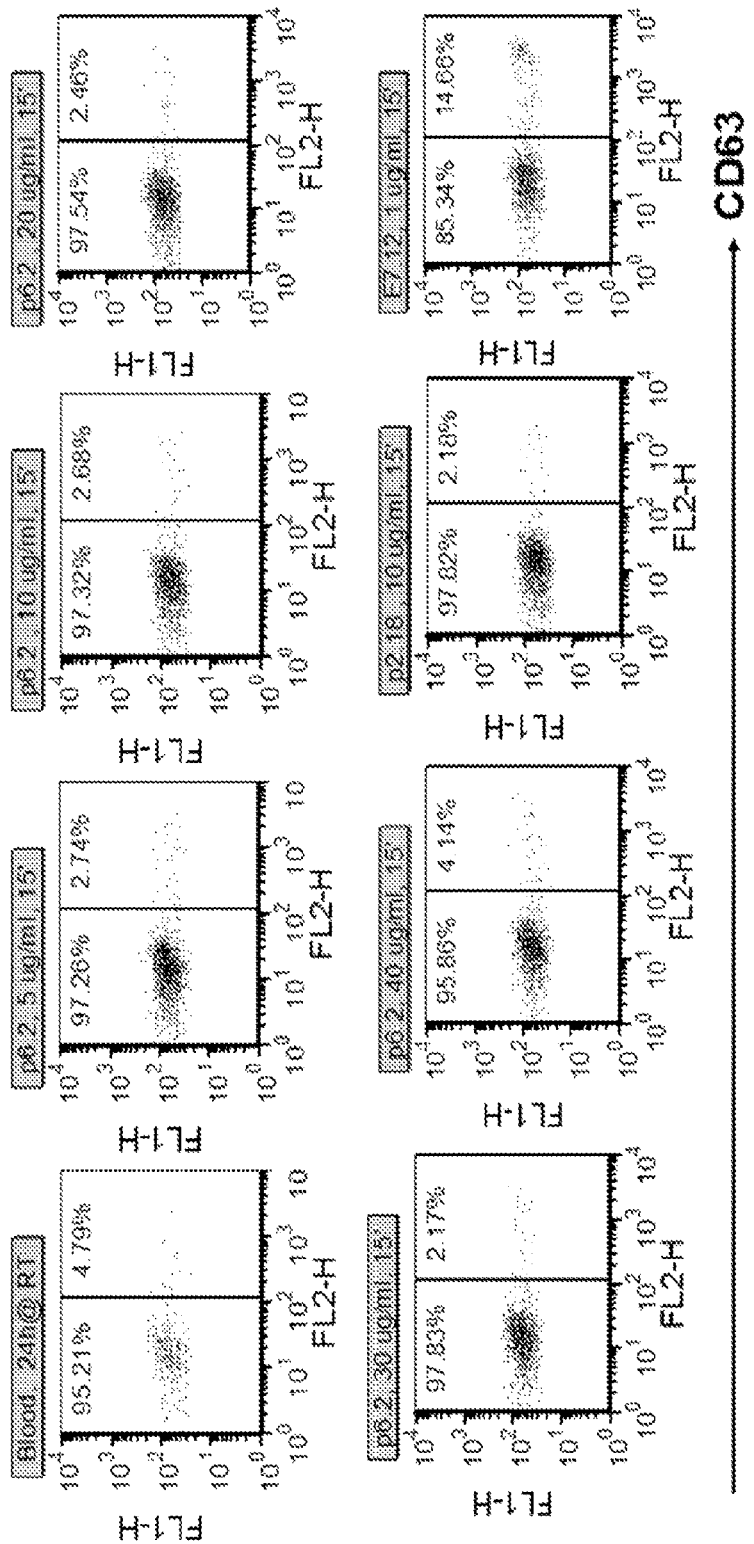
FIG. 2 shows flow cytometry data obtained from a basophil activation (BAT) assay, indicating that an example antibody according to one embodiment of the present disclosure does not activate basophils across a dose range of from 5 to 40 µg/ml.

The terms "antibodies" and "immunoglobulin" include antibodies or immunoglobulins of any isotype, whole antibodies (e.g., antibodies composed of a tetramer which in turn is composed of two dimers of a heavy and light chain polypeptide); half antibodies; single chain antibodies; fragments of antibodies (e.g., fragments of whole, half, or single chain antibodies) which retain specific binding to IgE, including, but not limited to Fab, Fv, scFv, and diabodies; chimeric antibodies; humanized antibodies (e.g., humanized whole antibodies, humanized half antibodies, or humanized antibody fragments); and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the terms are Fab', Fv, F(ab')$_2$, and or other antibody fragments that retain specific binding to antigen, and monoclonal antibodies. An antibody may be monovalent (e.g., in the case of a half antibody) or bivalent.

"Antibody fragments" comprise a portion of an intact antibody, for example, the antigen binding or variable region of the intact antibody. Examples of antibody fragments include, but are not limited to, a Fab, Fab', F(ab')$_2$, and Fv fragments; diabodies; linear antibodies (Zapata et al., Protein Eng. 8(10): 1057-1062 (1995)); and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

A "half antibody" refers to an antibody composed of a dimer of a heavy chain polypeptide and a light chain polypeptide, which heavy and light chains may be joined by noncovalent and/or covalent (e.g., disulfide) bonds. The half antibody may include a heavy chain that includes a human heavy chain constant region, and a light chain that includes a human light chain constant region. As opposed to a "full" or "complete" antibody that consists of two identical heavy chains and two identical light chains—and accordingly has two identical antigen binding sites—a half antibody has a single antigen binding site (i.e., is monovalent). As described in greater detail below, a half antibody may be generated by genetically modifying a nucleic acid that encodes the heavy chain of an anti-IgE antibody, e.g., by substituting one or more heavy chain amino acid residues (e.g., one, two, or more cysteines) that promote heavy chain dimerization for amino acids that do not promote (e.g., prevent) such dimerization, or post-translationally modifying one or more heavy chain amino acid residues (e.g., one, two, or more cysteines) that promote heavy chain dimerization such that the amino acid(s) are no longer capable of interacting with the residues of a different heavy chain.

"Monovalent" when used in the context of an antibody refers to an antibody that contains a single antigen-binding region. "Divalent" when used in the context of an antibody refers to an antibody that contains two antigen-binding regions.

"Fv" comprises the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the V$_H$-V$_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain (CH$_1$) of the heavy chain. Fab fragments differ from Fab' fragments by the addition of a few residues at the carboxyl terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2.

"Single-chain Fv" or "sFv" antibody fragments comprise the V$_H$ and V$_L$ domains of an antibody, where these domains are present in a single polypeptide chain. In some embodiments, the Fv polypeptide further comprises a polypeptide linker between the V$_H$ and V$_L$ domains, which enables the sFv to form the desired structure for antigen binding.

The term "diabodies" refers to small antibody fragments with two antigen-binding sites, which fragments comprise a heavy-chain variable domain (V$_H$) connected to a light-chain variable domain (V$_L$) in the same polypeptide chain (V$_H$-V$_L$). By using a linker that is too short to allow pairing between the two domains on the same chain, the domains are forced to pair with the complementary domains of another chain and create two antigen-binding sites. See, e.g., Hollinger et al., *Proc. Natl. Acad. Sci. USA*, 90:6444-6448 (1993).

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges.

A subject anti-IgE binds specifically to an epitope within an IgE polypeptide. Non-specific binding would refer to binding with an affinity of less than about $10^{-7}$ M, e.g., binding with an affinity of $10^{-6}$ M, $10^{-5}$ M, $10^{-4}$ M, etc.

By "CDR" or "complementarity determining region" is meant the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

CDR Definitions

| | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or non-reducing conditions using Coomassie blue or silver stain. Isolated antibody includes the antibody in situ within recombinant cells since at least one component of the antibody's natural environment will not be present. In some instances, isolated antibody will be prepared by at least one purification step.

The terms "individual," "subject," "host," and "patient," used interchangeably herein, refer to a mammal, including, but not limited to, rats, mice, non-human primates, humans, canines, felines, ungulates (e.g., equines, bovines, ovines, porcines, caprines), etc.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. In some cases, a biological sample will include mast cells, basophils, eosinophils, B cells, and the like.

The terms "type-I allergic reaction," "immediate hypersensitivity," "atopic allergy," "type-I hypersensitivity," and the like, as used herein, refer to the physiological response that occurs when an antigen entering the body encounters mast cells or basophils which have been sensitized by IgE attached to its high-affinity receptor, FcεRI on these cells. When an allergen reaches the sensitized mast cell or basophil, it cross-links surface-bound IgE, causing an increase in intracellular calcium (Ca2+) that triggers the release of pre-formed mediators, such as histamine and proteases, and newly synthesized, lipid-derived mediators such as leukotrienes and prostaglandins. These autocoids produce the clinical symptoms of allergy. In addition, cytokines, e.g., IL-4, TNF-alpha, are released from degranulating basophils and mast cells, and serve to augment the inflammatory response that accompanies an IgE reaction (see, e.g., Immunology, Fifth Edition, Roitt et al., eds., 1998, pp. 302-317). The specific manifestations of the hypersensitivity reaction in the sensitive or allergic subject depends on the site of the allergen exposure, the dose of allergen exposure, the reactivity of the organs in the subject (e.g., over-reactive lungs or nose) and the full panoply of the immune response to the allergen in that subject.

Symptoms and signs associated with type I hypersensitivity responses are extremely varied due to the wide range of tissues and organs that can be involved. These symptoms and signs can include, but are not limited to: itching of the skin, eyes, and throat, swelling and rashes of the skin (angioedema and urticaria/hives), hoarseness and difficulty breathing due to swelling of the vocal cord area, a persistent bumpy red flaking rash that may occur anywhere on the body, shortness of breath and wheezing (from tightening of the muscles in the airways and plugging of the airways, i.e., bronchoconstriction) in addition to increased mucus and fluid production, chest tightness and pain due to construction of the airway muscles, nausea, vomiting diarrhea, dizziness and fainting from low blood pressure, a rapid or irregular heartbeat and even death as a result of airway and/or cardiac compromise.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an antibody" or "a half antibody" includes a plurality of such antibodies or half antibodies and reference to "the CDR" includes reference to one or more CDRs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides antibodies that specifically bind to circulating and receptor-bound IgE and inhibit IgE-mediated cell activation. The antibodies are useful in various treatment, diagnostic, and monitoring applications, which are also provided.

Antibodies

Anti-IgE antibodies of the present disclosure specifically bind to an immunoglobulin E (IgE) polypeptide. In certain embodiments, the antibody specifically binds to "circulating" or "free" IgE and also to receptor-bound IgE. For example, in certain aspects, the anti-IgE antibody specifically binds to IgE regardless of whether the IgE is bound to the high affinity IgE receptor (FcεRI).

According to certain embodiments, an antibody of the present disclosure exhibits low affinity binding to IgE. By "low affinity" is meant the antibody or IgE binding fragment thereof specifically binds to IgE with an affinity of from $1\times10^{-5}$ M to $1\times10^{-9}$ M Kd, such as from $1\times10^{-5}$M to $1\times10^{-6}$M Kd, from $1\times10^{-6}$M to $1\times10^{-7}$M Kd, from $1\times10^{-7}$M to $1\times10^{-8}$M Kd, or from $1\times10^{-8}$M to $1\times10^{-9}$M Kd. For example, antibody P6.2 (see Examples section below) specifically binds to IgE with low affinity (Kd=$2.54\times10^{-6}$ M). Without being bound by theory, it is believed that certain advantageous therapeutic properties (see Table 3 below) of low affinity antibodies of the present disclosure which bind to circulating and surface-bound IgE (e.g., antibody P6.2 and the like) derives, at least in part, from the low affinity of the antibodies rendering free (serum) IgE as a reservoir (rather than a "sink") for the antibodies upon administration to a patient in need thereof. That is, given their low affinity, the antibodies may dissociate from the antibody-IgE serum complex and function as active drug (e.g., for binding to FcεRI-bound IgE on the surface of basophils, mast cells, eosinophils, and/or the like).

In certain aspects, an antibody or antigen binding fragment thereof of the present disclosure does not bind to IgE with high affinity. For example, in some embodiments, the antibody or antigen binding fragment thereof binds to IgE with an affinity that is less than $1.44\times10^{-10}$ M, which is the affinity at which antibody CIA-E-7.12 (ATCC Accession No. HB-236) binds to IgE.

According to certain embodiments, the antibody does not compete for IgE binding with the antibody CIA-E-7.12 (ATCC Accession No. HB-236).

Antibodies of the present disclosure may inhibit activation (e.g., degranulation) of effector cells that express FcεRI, such as mast cells, basophils, eosinophils, and the like. In certain aspects, the antibody inhibits activation (e.g., degranulation) of an effector cell by binding to FcεRI-bound IgE. According to one embodiment, an antibody of the present disclosure—upon binding to receptor-bound IgE—does not itself result in cell activation (e.g., does not result in crosslinking of neighboring IgE-FcεRI complexes).

In certain aspects, an anti-IgE antibody or IgE binding fragment thereof of the present disclosure specifically binds to circulating and receptor-bound IgE, binds to IgE with low affinity as defined herein (e.g., from $1\times10^{-5}$ M to $1\times10^{-9}$ M Kd) and inhibits activation of cells that express the high affinity IgE receptor (FcεRI).

According to certain embodiments, an anti-IgE antibody or IgE binding fragment thereof of the present disclosure specifically binds to circulating and receptor-bound IgE, does not compete for IgE binding with the antibody CIA-E-7.12 (ATCC Accession No. HB-236), and inhibits activation of cells that express the high affinity IgE receptor (FcεRI).

In certain aspects, an anti-IgE antibody or IgE binding fragment thereof of the present disclosure reduces the amount of IgE bound to the surface of cells that express the high affinity IgE receptor (FcεRI). According to certain embodiments, an antibody of the present disclosure reduces the amount of surface-bound IgE by triggering internalization of IgE (e.g., which may be present as an IgE-FcεRI complex) by the effector cell (e.g., a basophil, mast cell, eosinophil, and/or the like).

According to certain embodiments, an anti-IgE antibody or IgE binding fragment thereof of the present disclosure reduces the amount of high affinity IgE receptor (FcεRI) on the surface of cells (e.g., effector cells). Such antibodies may, for example, reduce the amount of surface FcεRI by triggering internalization of FcεRI (e.g., which may be present as an IgE-FcεRI complex) by the effector cell (e.g., a basophil, mast cell, eosinophil, and/or the like).

In certain aspects, an anti-IgE antibody or IgE binding fragment thereof of the present disclosure activates piecemeal degranulation in effector cells (e.g., a basophil, mast cell, eosinophil, and/or the like). In "piecemeal degranulation," granule proteins are mobilized and released by a mechanism that: (i) does not involve the wholesale secretion of granule content like in exocytosis; (ii) leaves behind partially empty membrane-bound granule chambers; and (iii) depends on the trafficking of small vesicles. See, e.g., Bandeira-Melo & Weller (2005) *Mem. Inst. Oswaldo Cruz* 100 (Supp. I):73-81. Piecemeal degranulation is associated with allergic/effector cell desensitization, but not anaphylactic degranulation. According to certain embodiments, an antibody of the present disclosure activates piecemeal degranulation, but not anaphylactic degranulation, in the effector cells (e.g., basophils, mast cells, eosinophils, and/or the like). Suitable approaches for determining whether an antibody activates piecemeal degranulation are known and include, e.g., assaying for up-regulation of CD203c in cells exposed to the antibody.

In certain aspects, an anti-IgE antibody or IgE binding fragment thereof of the present disclosure that binds to circulating and receptor-bound IgE also binds to membrane IgE (or "mIgE"). IgE exists in a B cell membrane-anchored form (membrane IgE) and in several secreted forms. See Zhang, K., Max, E. E., Cheah, H-K., and Saxon, A. (1994) *J. Biol. Chem.* 269:456-462. These distinct forms are splice variants. The main secreted form of IgE is generally a shorter form with the Fc region essentially terminating at the Cε4 domain, whereas membrane IgE includes additional C-terminal residues including the peptides encoded by the exons known as M1/M1' and M2. An anti-IgE antibody of the present disclosure may bind to any epitope of mIgE that is also available for binding in circulating and receptor-bound IgE. For example, the anti-IgE antibody may bind to an epitope in any of the Cε1, Cε2, Cε3, or Cε4 domains available for binding in circulating, receptor-bound and membrane IgE. In binding to membrane IgE, the antibody may inhibit IgE production, e.g., by inhibiting the maturation of IgE-expressing B cells.

The epitope of an antibody of the present disclosure may be present in any suitable region of IgE, so long as the epitope is accessible for binding when the IgE is receptor-bound (e.g., bound to FcεRI or FcεRII (CD23)). Details regarding the structure of IgE are found in Zheng et al. (*Biochemistry* (1991) 30:9125-9132), Wan et al. (*Nature Immunology* (2002) 3:681-686) and Gould and Sutton (*Nature Reviews Immunology* (2008) 8:205-217), the disclosures of which are incorporated herein by reference in their entireties for all purposes. The heavy ε-chain of IgE may be divided into five domains, which from C-terminus to N-terminus include: the Cε4 domain, the Cε3 domain, the Cε2 domain, the Cε81 domain, and the variable heavy chain region/domain (VH). An antibody according to the present disclosure may recognize an epitope, e.g., in the Cε4 domain, the Cε3 domain, the Cε2 domain, or the Cε81 domain of IgE. In certain aspects, the antibody does not recognize an epitope in the Cε3 domain of human IgE.

As summarized above, in certain aspects, an anti-IgE antibody or IgE binding fragment thereof of the present disclosure does not compete for IgE binding with the antibody CIA-E-7.12 (ATCC Accession No. HB-236)("E-7.12"). Competitive binding assays for determining whether two antibodies compete for binding to an antigen are known in the art, and an example enzyme-linked immunosorbent assay (ELISA)-based approach is described herein in the Examples section. That the antibody of the present disclosure does not competitively bind with the E-7.12 antibody indicates that the two antibodies do not share the same IgE epitope.

According to certain embodiments, an anti-IgE antibody of the present disclosure specifically binds to circulating and receptor-bound IgE and inhibits antigen-mediated (e.g., allergen-mediated) activation (e.g., degranulation) of effector cells that express the high affinity IgE receptor (FcεRI), such as basophils, mast cells, and/or eosinophils. For example, the antibody can inhibit effector cell activation by 5% or more, 10% or more, 15% or more, 20% or more, 25% or more, 30% or more, 40% or more, 50% or more, 60% or more, 70% or more, 80% or more, 90% or more, or 95% or more, compared to the degree of effector cell activation in the absence of the antibody. Effector cell activation may be determined using any convenient approach for the effector cell of interest, including the basophil activation test (BAT) and Passive Cutaneous Anaphylaxis (PCA) assay, described below in more detail in the Examples section. In certain aspects, the anti-IgE antibody of the present disclosure blocks or reduces effector cell activation when present at concentrations of from 0.01 to 5 µg/ml, such as from 0.03 to 2.5 µg/ml, e.g., 0.05 to 1 µg/ml.

According to one embodiment, an anti-IgE antibody of the present disclosure specifically binds to circulating and receptor-bound IgE, does not compete for IgE binding with the antibody CIA-E-7.12 (ATCC Accession No. HB-236), and reduces or eliminates antigen-mediated (e.g., allergen-mediated) crosslinking of neighboring IgE/FcεRI complexes on the surface of an effector cell, e.g., such as a basophil, mast cell or eosinophil. For example, the antibody may reduce crosslinking of neighboring IgE/FcεRI complexes by 5% or more, 10% or more, 15% or more, 20% or more, 25% or more, 30% or more, 40% or more, 50% or more, 60% or more, 70% or more, 80% or more, 90% or more, or 95% or more, compared to the degree of IgE/FcεRI complex crosslinking in the absence of the antibody.

Antibodies of the present disclosure may include one or more (e.g., one or two) heavy chain variable regions (VH) and/or one or more (e.g., one or two) light chain variable regions (VL), or subfragments thereof capable of binding to an epitope. The VH and VL regions can be further subdivided into regions of hypervariability, termed "complementarity determining regions (CDR)", interspersed with regions that are more conserved, termed "framework regions (FR)". The extent of the FR and CDRs has been precisely defined (see, Kabat, et al. (1991) Sequences of Proteins of Immunological Interest, Fifth Edition, U.S. Department of Health and Human Services, NIH Publication No. 91-3242; Chothia et al. (1987) J. Mol. Biol. 196: 901-917). A VH can comprise three CDRs and four FRs arranged from N-terminus to C-terminus in the following order: FR1, CDR1, FR2, CDR2, FR3, CDR3, FR4. Similarly, a VL can comprise three CDRs and four FRs arranged from N-terminus to C-terminus in the following order: FR1, CDR1, FR2, CDR2, FR3, CDR3, FR4.

The VH or VL chain of an antibody can further include all or part of a heavy or light chain constant region, to thereby form a heavy or light immunoglobulin chain, respectively. In one embodiment, the antibody is a tetramer of two heavy and two light chains, wherein the heavy and light chains are interconnected by, for example, disulfide bonds. The heavy chain constant region is comprised of three domains, CH1, CH2 and CH3. The light chain constant region is comprised of one domain, CL. The variable regions of the heavy and light chains comprise binding regions that interact with antigen. The constant regions of the antibodies typically mediate the binding of the antibody to host tissues and factors, including various cells of the immune system and the first component of the complement system. The term "antibody" includes intact immunoglobulins of types IgA, IgG, IgE, IgD, IgM and subtypes thereof. In some embodiments, the antibody is an IgG isotype (e.g., an IgG1 isotype).

The term "immunoglobulin" may refer to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes; and numerous immunoglobulin variable region genes. Full-length immunoglobulin light chains (about 25 kD or 214 amino acids) are encoded by a variable region gene at the N-terminus (about 110 amino acids) and a kappa or lambda constant region at the C-terminus. Full-length immunoglobulin heavy chains (about 50 kD or 446 amino acids) are encoded by a variable region gene at the N-terminus (about 116 amino acids) and one of the other aforementioned constant region genes at the C-terminus, e.g. gamma (encoding about 330 amino acids). In some embodiments, an antibody of the present disclosure comprises a full-length immunoglobulin heavy chain and a full-length immunoglobulin light chain.

In some embodiments, an antibody of the present disclosure does not comprise a full-length immunoglobulin heavy chain and a full-length immunoglobulin light chain, but instead comprises antigen-binding fragments of a full-length immunoglobulin heavy chain and/or a full-length immunoglobulin light chain. In some embodiments, the antigen-binding fragments are contained on separate polypeptide chains; in other embodiments, the antigen-binding fragments are contained within a single polypeptide chain. The term "antigen-binding fragment" refers to one or more fragments of a full-length antibody according to any of the embodiments described elsewhere herein. For example, in certain aspects, the IgE binding fragment specifically binds to circulating and receptor-bound IgE, binds to IgE with low affinity as defined herein (e.g., from $1 \times 10^{-5}$ M to $1 \times 10^{-9}$ M) and inhibits activation of cells that express the high affinity IgE receptor (FcɛRI). According to certain embodiments, the IgE binding fragment specifically binds to circulating and receptor-bound IgE, does not compete for IgE binding with the antibody CIA-E-7.12 (ATCC Accession No. HB-236), and inhibits activation of cells that express the high affinity IgE receptor (FcɛRI).

Examples of binding fragments include (i) a Fab fragment (a monovalent fragment consisting of the VL, VH, CL and CH1 domains); (ii) a F(ab')$_2$ fragment (a bivalent fragment comprising two Fab fragments linked by a disulfide bridge at the hinge region); (iii) a Fd fragment (consisting of the VH and CH1 domains); (iv) a Fv fragment (consisting of the VH and VL domains of a single arm of an antibody); (v) a dAb fragment (consisting of the VH domain); (vi) an isolated CDR; (vii) a single chain Fv (scFv) (consisting of the VH and VL domains of a single arm of an antibody joined by a synthetic linker using recombinant means such that the VH and VL domains pair to form a monovalent molecule); (viii) diabodies (consisting of two scFvs in which the VH and VL domains are joined such that they do not pair to form a monovalent molecule; the VH of each one of the scFv pairs with the VL domain of the other scFv to form a bivalent molecule); (ix) bi-specific antibodies (consisting of at least two antigen binding regions, each region binding a different epitope). In some embodiments, the antibody fragment is a Fab fragment or is a single-chain antibody (scFv).

In certain aspects, an antibody of the present disclosure is a recombinant or modified antibody, e.g., a chimeric, humanized, deimmunized, and/or an in vitro generated antibody. The term "recombinant" or "modified" antibody as used herein is intended to include all antibodies that are prepared, expressed, created, or isolated by recombinant means, such as (i) antibodies expressed using a recombinant expression vector transfected into a host cell; (ii) antibodies isolated from a recombinant, combinatorial antibody library; (iii) antibodies isolated from an animal (e.g. a mouse) that is transgenic for human immunoglobulin genes; or (iv) antibodies prepared, expressed, created, or isolated by any other means that involves splicing of human immunoglobulin gene sequences to other DNA sequences. Such recombinant antibodies include humanized, CDR grafted, chimeric, deimmunized, and in vitro generated antibodies; and can optionally include constant regions derived from human germline immunoglobulin sequences.

In certain aspects, an anti-IgE antibody or IgE binding fragment thereof of the present disclosure competes for specific binding to IgE with an antibody or fragment thereof that includes one or more of the complementary determining regions (CDRs) of SEQ ID NOs:1-6 provided in Table 2 below. The CDRs of SEQ ID NOs:1-6 are the CDRs of antibody p6.2 described below in more detail. For example, an antibody of the present disclosure may compete for binding to IgE with an antibody that includes one, two, three, four, five, or all six of the CDRs set forth as SEQ ID NOs:1-6 in Table 2. According to one embodiment, an antibody of the present disclosure competes for specific binding to IgE with an antibody or fragment thereof that includes a heavy chain complementary determining region 1 (HCDR1) having the amino acid sequence of SEQ ID NO:1; a heavy chain complementary determining region 2 (HCDR2) having the amino acid sequence of SEQ ID NO:2; a heavy chain complementary determining region 3 (HCDR3) having the amino acid sequence of SEQ ID NO:3; a light chain complementary determining region 1 (LCDR1) having the amino acid sequence of SEQ ID NO:4; a light chain complementary determining region 2 (LCDR2) having the amino acid sequence of SEQ ID NO:5; and a light chain complementary determining region 3 (LCDR3) having the amino acid sequence of SEQ ID NO:6.

According to certain embodiments, an anti-IgE antibody or IgE binding fragment thereof of the present disclosure includes a complementary determining region selected from: a heavy chain complementary determining region 1 (HCDR1) having the amino acid sequence of SEQ ID NO:1; a heavy chain complementary determining region 2 (HCDR2) having the amino acid sequence of SEQ ID NO:2; a heavy chain complementary determining region 3 (HCDR3) having the amino acid sequence of SEQ ID NO:3; a light chain complementary determining region 1 (LCDR1) having the amino acid sequence of SEQ ID NO:4; a light chain complementary determining region 2 (LCDR2) having the amino acid sequence of SEQ ID NO:5; a light chain complementary determining region 3 (LCDR3) having the amino acid sequence of SEQ ID NO:6; and any combination thereof. In certain aspects, the anti-IgE antibody or IgE binding fragment thereof includes all six of the CDRs set forth in SEQ ID NOs:1-6.

In certain aspects, an anti-IgE antibody or IgE binding fragment thereof of the present disclosure includes a heavy chain polypeptide comprising a variable region having an amino acid sequence that is 60% or more, 65% or more, 70% or more, 75% or more, 80% or more, 85% or more, or 95% or more (e.g., 100%) identical to the heavy chain variable region set forth in SEQ ID NO:7. According to certain embodiments, an anti-IgE antibody or IgE binding fragment thereof of the present disclosure includes a light chain polypeptide comprising a variable region having an amino acid sequence that is 60% or more, 65% or more, 70% or more, 75% or more, 80% or more, 85% or more, or 95% or more (e.g., 100%) identical to the light chain variable region set forth in SEQ ID NO:8. Also provided are anti-IgE antibodies or IgE binding fragments thereof that include: a heavy chain polypeptide comprising a variable region having an amino acid sequence that is 60% or more, 65% or more, 70% or more, 75% or more, 80% or more, 85% or more, or 95% or more (e.g., 100%) identical to the heavy chain variable region set forth in SEQ ID NO:7; and a light chain polypeptide comprising a variable region having an amino acid sequence that is 60% or more, 65% or more, 70% or more, 75% or more, 80% or more, 85% or more, or 95% or more (e.g., 100%) identical to the light chain variable region set forth in SEQ ID NO:8.

TABLE 2

| | | |
|---|---|---|
| P6.2 V$_H$ CDR1 | NYLIE (SEQ ID NO: 1) | |
| P6.2 V$_H$ CDR2 | VINPGSGFTKYNEKFKG (SEQ ID NO: 2) | |
| P6.2 V$_H$ CDR3 | EDVYSWFAYWGQGTLVTVSA (SEQ ID NO: 3) | |
| P6.2 V$_L$ CDR1 | RASESVDSYGNSFMH (SEQ ID NO: 4) | |
| P6.2 V$_L$ CDR2 | RTSNLES (SEQ ID NO: 5) | |
| P6.2 V$_L$ CDR3 | QQSYEDPFTFGSGTKLEIK (SEQ ID NO: 6) | |
| P6.2 V$_H$ | QVQLQQSGAELVRPGTSVKVSCKASGYAFT<u>NYLIE</u><br>WVKQRPGQGLEWIG<u>VINPGSGFTKYNEKFKG</u>KATL<br>TADKSSSTAYMHLSSLTSDDSAVYFCAR<u>EDVYSWF</u><br><u>AYWGQGTLVTVSA</u> (SEQ ID NO: 7) | |
| P6.2 V$_L$ | DIVLTQSPASLAVSLGQRATISC<u>RASESVDSYGNS</u><br><u>FMH</u>WYQQKPGQPPKLLIY<u>RTSNLES</u>GIPARFSGSG<br>SRTDFTLTINPVEADDVATYFC<u>QQSYEDPFTFGSG</u><br><u>TKLEIK</u> (SEQ ID NO: 8) | |
| P6.2 V$_H$ nt | CAGGTCCAGCTGCAGCAGTCTGGAGCTGAGCTGGT<br>AAGGCCTGGGACTTCAGTGAAGGTGTCCTGCAAGG<br>CTTCTGGATACGCCTTCACTAATTACTTGATAGAG<br>TGGGTAAAGCAGAGGCCTGGACAGGGCCTTGAGTG<br>GATTGGAGTGATTAATCCTGGAAGTGGTTTTACAA<br>AATACAATGAGAAGTTCAAGGGCAAGGCAACACTG<br>ACTGCAGACAAATCCTCCAGCACTGCCTACATGCA<br>CCTCAGCAGCCTGACATCTGATGACTCTGCGGTCT<br>ATTTCTGTGCAAGAGAAGATGTTTACTCCTGGTTT<br>GCTTACTGGGGCCAAGGGACTCTGGTCACTGTCTC<br>TGCA (SEQ ID NO: 9) | |
| P6.2 V$_L$ nt | GACATTGTGCTGACCCAATCTCCAGCTTCTTTGGC<br>TGTGTCTCTAGGGCAGAGGGCCACCATATCCTGCA<br>GAGCCAGTGAAAGTGTTGATAGTTATGGCAATAGT<br>TTTATGCACTGGTACCAGCAGAAACCAGGACAGCC<br>ACCCAAACTCCTCATCTATCGTACATCCAACCTAG<br>AATCTGGGATCCCTGCCAGGTTCAGTGGCAGTGGG<br>TCTAGGACAGACTTCACCCTCACCATTAATCCTGT<br>GGAGGCTGATGATGTTGCAACCTATTTCTGTCAGC<br>AAAGTTATGAGGATCCATTCACGTTCGGCTCGGGG<br>ACAAAGTTGGAAATAAAA (SEQ ID NO: 10) | |

Aspects of the present disclosure include an anti-IgE antibody or IgE binding fragment thereof that reduces the amount of IgE bound to the surface of cells that express the high affinity IgE receptor (FcεRI), when such cells are exposed to the antibody present at a suitable concentration. According to certain embodiments, the antibody reduces the amount of IgE on the surface of cells that express FcεRI by 10% or more, 20% or more, 30% or more, 40% or more, 50% or more, 60% or more, 70% or more, 80% or more, 90% or more, or 95% or more, as compared to the amount of IgE bound to the surface of the cells in the absence of the antibody. In certain aspects, the antibody is capable of reducing the amount of IgE bound to the surface of the cells when present at a concentration of from 0.01 to 10 μg/ml, such as 0.05 to 5 μg/ml, e.g., 0.1 to 2 μg/ml.

An anti-IgE antibody or IgE binding fragment thereof of the present disclosure may be "humanized." The term "humanized antibody" refers to immunoglobulins, half antibodies, immunoglobulin chains or fragments thereof (such as Fv, scFv, Fab, Fab', F(ab')2 or other antigen-binding subsequences of antibodies) which contain minimal sequence derived from non-human immunoglobulin. The humanized antibodies may be human immunoglobulins (recipient antibody) in which residues from a complementary determining region (CDR) of the recipient are replaced by residues from a CDR of a non-human species (donor antibody) such as mouse, rat or rabbit having the desired specificity (e.g., specificity for circulating and receptor-bound IgE, and not competing with antibody E7.12 for binding to IgE), affinity and capacity. In some instances, Fv framework residues of the human immunoglobulin are replaced by corresponding non-human residues. Furthermore, a humanized antibody may comprise residues which are found neither in the recipient antibody nor in the imported CDR or framework sequences. See, Queen et al., Proc. Natl. Acad. Sci. USA 86:10029 10033 (1989), U.S. Pat. Nos. 5,530,101, 5,585,089, 5,693,761, WO 90/07861, and U.S. Pat. No. 5,225,539. Methods of making humanized antibodies are known in the art. See, e.g., U.S. Pat. No. 7,256,273. According to one embodiment, the anti-IgE antibody or IgE binding fragment thereof of the present disclosure is a humanized monoclonal anti-IgE antibody or half antibody that: specifically binds to circulating and receptor-bound IgE; does not compete for IgE binding with the antibody CIA-E-7.12 (ATCC Accession No. HB-236); and inhibits activation of cells (e.g., mast cells, basophils, eosinophils, and the like) that express the high affinity IgE receptor (FcεRI).

The substitution of mouse CDRs into a human variable domain framework can result in retention of their correct spatial orientation where, e.g., the human variable domain framework adopts the same or similar conformation to the mouse variable framework from which the CDRs originated. This can be achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., Protein Engineering 4:773 (1991); Kolbinger et al., Protein Engineering 6:971 (1993).

Having identified the complementarity determining regions of the donor (e.g., murine) immunoglobulin and appropriate human acceptor immunoglobulins, generating a humanized antibody may include determining which, if any, residues from these components should be substituted to optimize the properties of the resulting humanized antibody. In general, substitution of human amino acid residues with murine residues should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIACORE) and/or solid-phase ELISA analysis. In many embodiments, a subject humanized antibody does not substantially elicit a HAMA response in a human subject.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, may lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

CDR and framework regions are as defined by Kabat, Sequences of Proteins of Immunological Interest (National Institutes of Health, Bethesda, Md., 1987 and 1991). An alternative structural definition has been proposed by Chothia et al., J. Mol. Biol. 196:901 (1987); Nature 342:878 (1989); and J. Mol. Biol. 186:651 (1989) (collectively referred to as "Chothia"). When framework residues, as defined by Kabat, supra, constitute structural loop residues as defined by Chothia, supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk J M B 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233:747 (1986)) and selecting these amino acids from the donor may be desirable to keep all the antigen contacts that provide affinity in the original antibody.

In some embodiments, an anti-IgE antibody of the present disclosure comprises scFv multimers. For example, in some embodiments, a subject antibody is an scFv dimer (e.g., comprises two tandem scFv (scFv$_2$)), an scFv trimer (e.g., comprises three tandem scFv (scFv$_3$)), an scFv tetramer (e.g., comprises four tandem scFv (scFv$_4$)), or is a multimer of more than four scFv (e.g., in tandem). The scFv monomers can be linked in tandem via linkers of from about 2 amino acids to about 10 amino acids in length, e.g., 2 aa, 3 aa, 4 aa, 5 aa, 6 aa, 7 aa, 8 aa, 9 aa, or 10 aa in length. Suitable linkers include, e.g., (Gly)$_x$, where x is an integer from 2 to 10. Other suitable linkers are those discussed above. In some embodiments, each of the scFv monomers in a subject scFV multimer is humanized, as described above.

In certain aspects, an anti-IgE antibody of the present disclosure comprises a constant region of an immunoglobulin (e.g., an Fc region). The Fc region, if present, can be a human Fc region. If constant regions are present, the antibody can contain both light chain and heavy chain constant regions. Suitable heavy chain constant region include CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. An example of a suitable heavy chain Fc region is a human isotype IgG1 Fc. Light chain constant regions can be lambda or kappa. An anti-IgE antibody of the present disclosure can comprise sequences from more than one class or isotype. Antibodies can be expressed as tetramers containing two light and two heavy chains, as half antibodies, as separate heavy chains, light chains, as Fab, Fab' F(ab')2, and Fv, or as single chain antibodies in which heavy and light chain variable domains are linked through a spacer.

In some embodiments, an anti-IgE antibody of the present disclosure comprises a free thiol (—SH) group at the carboxyl terminus, where the free thiol group can be used to attach the antibody to a second polypeptide (e.g., another antibody, including a subject antibody), a scaffold, a carrier, etc.

In certain aspects, an anti-IgE antibody of the present disclosure includes one or more non-naturally occurring amino acids. In some embodiments, the non-naturally encoded amino acid comprises a carbonyl group, an acetyl group, an aminooxy group, a hydrazine group, a hydrazide group, a semicarbazide group, an azide group, or an alkyne group. See, e.g., Liu and Schultz (Annual Review of Biochemistry (2010) 79:413-44) for various non-naturally occurring amino acids and strategies for incorporating the same into a subject antibody, half antibody, antibody fragments, etc. Inclusion of a non-naturally occurring amino acid may be useful, e.g., to prevent heavy chain dimerization. For example, a cysteine residue in the hinge region of the heavy chain of a subject antibody may be replaced by a non-naturally occurring amino acid (e.g., via genetic engineering and incorporation using orthogonal translation components) that does not promote dimerization of the heavy chain with a second heavy chain. A "non-naturally encoded amino acid" refers to an amino acid that is not one of the 20 common amino acids or pyrrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex.

The present disclosure also provides anti-IgE antibodies having an attached moiety of interest, e.g. a detectable label, drug, toxin, half-life-extending moiety, and the like. Modification of antibodies can be accomplished by a variety of synthetic and/or recombinant methods. The moiety or moieties attached to an antibody can provide for one or more of a wide variety of functions or features. Example moieties include detectable labels (e.g., dye labels (e.g., chromophores, fluorophores), biophysical probes (spin labels, nuclear magnetic resonance (NMR) probes), Förster Resonance Energy Transfer (FRET)-type labels (e.g., at least one member of a FRET pair, including at least one member of a fluorophore/quencher pair), Bioluminescence Resonance Energy Transfer (BRET)-type labels (e.g., at least one member of a BRET pair), immunodetectable tags (e.g., FLAG, His(6), and the like); water soluble polymers (e.g., PEGylation); purification tags (e.g., to facilitate isolation by affinity chromatography (e.g., attachment of a FLAG epitope; membrane localization domains (e.g., lipids or glycophosphatidylinositol (GPI)-type anchors); immobilization tags (e.g., to facilitate attachment of the polypeptide to a surface, including selective attachment); drugs (e.g., to facilitate drug targeting, e.g., through attachment of the drug to an antibody); and the like.

An anti-IgE antibody of the present disclosure may be glycosylated, e.g., the antibody can include a covalently linked carbohydrate or polysaccharide moiety. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. Glycosylation can be accomplished by, for example, recombination production in a host cell having the desired glycosylation machinery.

Addition of glycosylation sites to an antibody may be accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of an antibody.

An anti-IgE antibody of the present disclosure may be covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker. Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one step reaction procedure in which the cross-linker is added to a solution containing a mixture of the polypeptides to be linked. Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidhexane (BMH), 1,5-difluoro-2,4-dinitrobenzene (DFDNB), and 1,4-di-(3',2'-pyridyldithio) propinoamido butane (DPDPB).

Heterobifunctional cross-linkers have two or more different reactive moieties (e.g., amine reactive moiety and a sulfhydryl-reactive moiety) and are cross-linked with one of the polypeptides via the amine or sulfhydryl reactive moiety, then reacted with the other polypeptide via the non-reacted moiety. Multiple heterobifunctional haloacetyl cross-linkers are available, as are pyridyl disulfide cross-linkers. Carbodiimides are a classic example of heterobifunctional cross-linking reagents for coupling carboxyls to amines, which results in an amide bond.

In certain aspects, an anti-IgE antibody of the present disclosure is immobilized on a solid support. Suitable supports are known in the art and comprise—inter alia—commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

According to certain embodiments, an anti-IgE antibody of the present disclosure includes a detectable label. Suitable detectable labels include any composition detectable by spectroscopic, photochemical, biochemical, immunochemical, electrical, optical or chemical means. Suitable include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^3$H, $^{125}$I, $^{35}$S, $^{14}$C, or $^{32}$P), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

Aspects of the present disclosure include an anti-IgE antibody that includes a contrast agent or a radioisotope, where the contrast agent or radioisotope is one that is suitable for use as a detectable label, e.g., in imaging, e.g., imaging procedures carried out on humans. Non-limiting examples of labels include radioisotope such as $^{123}$I (iodine), $^{18}$F (fluorine), $^{99}$Tc (technetium), $^{111}$In (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals.

An anti-IgE antibody of the present disclosure can be labeled using standard techniques. For example, the antibody can be iodinated using chloramine T or 1,3,4,6-tetrachloro-3α,6α-dephenylglycouril. For fluorination, fluorine is added to a subject antibody during the synthesis by a fluoride ion displacement reaction. See, Muller-Gartner, H., TIB Tech., 16:122-130 (1998) and Saji, H., Crit. Rev. Ther. Drug Carrier Syst., 16(2):209-244 (1999) for a review of synthesis of proteins with such radioisotopes. The antibody can also be labeled with a contrast agent through standard techniques. For example, the antibody can be labeled with Gd by conjugating low molecular Gd chelates such as Gd diethylene triamine pentaacetic acid (GdDTPA) or Gd tetraazacyclododecanetetraacetic (GdDOTA) to the antibody. See, Caravan et al., Chem. Rev. 99:2293-2352 (1999) and Lauffer et al., J. Magn. Reson. Imaging, 3:11-16 (1985). A subject antibody can be labeled with Gd by, for example, conjugating polylysine-Gd chelates to the antibody. See, for example, Curtet et al., Invest. Radiol., 33(10):752-761 (1998). Alternatively, the antibody can be labeled with Gd by incubating paramagnetic polymerized liposomes that include Gd chelator lipid with avidin and biotinylated antibody. See, for example, Sipkins et al., Nature Med., 4:623-626 (1998).

Suitable fluorescent proteins that can be linked to an anti-IgE antibody of the present disclosure include, but are not limited to, a green fluorescent protein from *Aequoria victoria* or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; a red fluorescent protein; a yellow fluorescent protein; any of a variety of fluorescent and colored proteins from Anthozoan species, as described in, e.g., Matz et al. (1999) *Nature Biotechnol.* 17:969-973; and the like.

According to certain embodiments, an anti-IgE antibody of the present disclosure includes a "radiopaque" label, e.g. a label that can be easily visualized using, for example, x-rays. Radiopaque materials of interest include iodide, bromide or barium salts. Other radiopaque materials are also known and include, but are not limited to organic bismuth derivatives (see, e.g., U.S. Pat. No. 5,939,045), radiopaque multiurethanes (see U.S. Pat. No. 5,346,981), organobismuth composites (see, e.g., U.S. Pat. No. 5,256,334), radiopaque barium multimer complexes (see, e.g., U.S. Pat. No. 4,866,132), and the like.

In certain aspects, an anti-IgE antibody of the present disclosure is linked to (e.g., covalently or non-covalently linked to) a fusion partner, e.g., a ligand; an epitope tag; a peptide; a protein other than an antibody; and the like. Suitable fusion partners include peptides and polypeptides that confer enhanced stability in vivo (e.g., enhanced serum half-life); provide ease of purification, and the like; provide for secretion of the fusion protein from a cell; provide an epitope tag, e.g., (His)n, e.g., 6His, and the like; provide for secretion of the fusion protein from a cell; provide an epitope tag, e.g., GST, hemagglutinin (HA; e.g., CYPYDVPDYA; SEQ ID NO:11), FLAG (e.g., DYKDDDDK; SEQ ID NO:12), c-myc (e.g., CEQKLISEEDL; SEQ ID NO:13), and the like; provide a detectable signal, e.g., an enzyme that generates a detectable product (e.g., β-galactosidase, luciferase), or a protein that is itself detectable, e.g., a green fluorescent protein, a red fluorescent protein, a yellow fluorescent protein, etc.; provides for multimerization, e.g., a multimerization domain such as an Fc portion of an immunoglobulin; and the like.

The fusion may also include an affinity domain, including peptide sequences that can interact with a binding partner, e.g., such as one immobilized on a solid support, useful for identification or purification. Consecutive single amino acids, such as histidine, when fused to a protein, can be used for one-step purification of the fusion protein by high affinity binding to a resin column, such as nickel sepharose. Examples of affinity domains include His5 (HHHHH) SEQ ID NO:14), HisX6 (HHHHHH) SEQ ID NO:15), C-myc (EQKLISEEDL) SEQ ID NO:16), Flag (DYKDDDDK) SEQ ID NO:12), StrepTag (WSHPQFEK) (SEQ ID NO:17), hemagglutinin, e.g., HA Tag (YPYDVPDYA; SEQ ID NO:18), glutathinone-S-transferase (GST), thioredoxin, cellulose binding domain, RYIRS (SEQ ID NO:19), Phe-His-His-Thr (SEQ ID NO:20), chitin binding domain, S-peptide, T7 peptide, SH2 domain, C-end RNA tag, WEAAAREACCRECCARA (SEQ ID NO:21), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, leucine zipper sequences, and maltose binding protein.

An anti-IgE antibody of the present disclosure may be modified to include a carbohydrate moiety, where the carbohydrate moiety can be covalently linked to the antibody. In some embodiments, the antibody is modified to include a lipid moiety, where the lipid moiety can be covalently linked to the antibody. Suitable lipid moieties include, e.g., an N-fatty acyl group such as N-lauroyl, N-oleoyl, etc.; a fatty amine such as dodecyl amine, oleoyl amine, etc.; a C3-C16 long-chain aliphatic lipid; and the like. See, e.g., U.S. Pat. No. 6,638,513). In some embodiments, the antibody is incorporated into a liposome.

Where an anti-IgE antibody of the present disclosure includes a covalently linked heterologous moiety, the heterologous moiety can be linked to the anti-IgE heavy and/or light chain directly or via a linker. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Examples of flexible linkers include glycine polymers (G)n, glycine-serine polymers (including, for example, (GS)n, GSGGSn (SEQ ID NO:22) and GGGSn (SEQ ID NO:23), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, Rev. Computational Chem. 11173-142 (1992)). Example flexible linkers include, but are not limited GGSG (SEQ ID NO:24), GGSGG (SEQ ID NO:25), GSGSG (SEQ ID NO: 26), GSGGG (SEQ ID NO: 27), GGGSG (SEQ ID NO: 28), GSSSG (SEQ ID NO: 29), and the like. The ordinarily skilled artisan will recognize that design of a peptide conjugated to any elements described above can include linkers that are all or partially flexible, such that the linker can include a flexible linker as well as one or more portions that confer less flexible structure.

Methods of Producing an Antibody

An anti-IgE antibody of the present disclosure may be produced by any known method, e.g., conventional synthetic methods for protein synthesis, recombinant DNA methods, etc.

Recombinant methods can be used for production of an anti-IgE antibody of the present disclosure. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

When the antibody is an anti-IgE half antibody, the half antibody may be generated by a method comprising genetically modifying a nucleic acid that encodes the light and/or heavy chain of an anti-IgE antibody. The genetic modification may include the substitution of one or more heavy chain amino acid residues that promote heavy chain dimerization (e.g., one or more cysteines in a hinge region of the antibody heavy chain) for amino acids that prevent such dimerization. In certain aspects, a subject antibody is an anti-IgE half antibody that comprises one or more (e.g., 1, 2, 3 or more) cysteine substitutions, where a cysteine residue is substituted for a non-cysteine natural or non-naturally occurring amino acid. For example, the half antibody may include one or more cysteine substitutions in a hinge region of the antibody heavy chain, e.g., two cysteine substitutions in the hinge region. The cysteines may be independently substituted for any suitable natural or non-natural amino acid, including but not limited to alanine, serine, etc. Recombinant DNA techniques for generating an antibody (e.g., a half antibody) that includes one or more desired amino acid substitutions are known in the art and described elsewhere herein.

Because of the degeneracy of the code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a polynucleotide encoding an anti-IgE antibody or IgE binding fragment thereof. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce the polypeptides of the present disclosure (e.g., polynucleotides encoding immunoglobulins or fragments thereof). See Winnacker, From Genes to Clones, VCH Publishers, N.Y., N.Y. (1987). Suitable mammalian host cells include CHO cell lines, various Cos cell lines, HeLa cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148: 1149 (1992).

Where an anti-IgE antibody of the present disclosure is a single chain polypeptide, it can be synthesized using standard chemical peptide synthesis techniques. Where a polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al., Solid Phase Peptide Synthesis, 2nd ed. Pierce Chem. Co., Rockford, Ill. (1984); and Ganesan A. 2006 *Mini Rev. Med Chem*. 6:3-10 and Camarero J A et al. 2005 *Protein Pept Lett*. 12:723-8. Briefly, small insoluble, porous beads are treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Once synthesized (either chemically or recombinantly), the whole antibodies, half antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Compositions

Aspects of the present disclosure include compositions including an anti-IgE antibody or IgE binding fragment thereof according to the present disclosure, e.g., an antibody having any of the characteristics described in the above section entitled "Antibodies", the Examples section, etc. An antibody composition of the present disclosure can include, in addition to an anti-IgE antibody or IgE binding fragment thereof, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

Nucleic Acids

The present disclosure provides nucleic acids comprising nucleotide sequences encoding an anti-IgE antibody or IgE binding fragment thereof, e.g., an antibody having any of the characteristics described in the above section entitled "Antibodies", the Examples section, etc. A nucleotide sequence encoding an anti-IgE antibody or IgE binding fragment thereof of the present disclosure can be operably linked to one or more regulatory elements, such as a promoter and enhancer, that allow expression of the nucleotide sequence in the intended target cells (e.g., a cell that is genetically modified to synthesize the encoded antibody).

Suitable promoter and enhancer elements are known in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (Lad repressor protein changes conformation when contacted with lactose, thereby preventing the Lad repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL 1 promoter, a GAL 10 promoter, an ADH2 promoter, a PHO5 promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC 1 promoter, a TRP 1 promoter, a URA3 promoter, a LEU2 promoter, an ENO promoter, a TP1 promoter, and AOX1 (e.g., for use in *Pichia*). Selection of the appropriate vector and promoter is within the level of ordinary skill in the art.

A nucleotide sequence encoding an anti-IgE antibody or IgE binding fragment thereof of the present disclosure can be present in an expression vector and/or a cloning vector. Where the antibody comprises two separate polypeptides, nucleotide sequences encoding the two polypeptides can be cloned in the same or separate vectors. An expression vector can include a selectable marker, an origin of replication, and other features that provide for replication and/or maintenance of the vector.

Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus; adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166: 154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

A nucleic acid of the present disclosure may include a nucleotide sequence encoding one or more chains of an anti-IgE antibody or IgE binding fragment thereof of the present disclosure. A subject nucleic acid can comprise a nucleotide sequence encoding anti-IgE heavy- and light-chains, as described above. According to certain embodiments, a nucleic acid of the present disclosure encodes one or more (e.g., each) of the CDRs (in any combination) set forth in SEQ ID NOs:1-6 shown above in Table 2. In certain aspects, the nucleic acid includes the nucleotide sequence of SEQ ID NO:9 (encoding the variable region of the heavy chain of antibody P6.2), SEQ ID NO:10 (encoding the variable region of the light chain of antibody P6.2), or the nucleotide sequences of SEQ ID NO:9 and SEQ ID NO:10.

Cells

The present disclosure provides isolated genetically modified host cells (e.g., in vitro cells) that are genetically modified with a nucleic acid of the present disclosure. In some embodiments, an isolated genetically modified host cell of the present disclosure can produce a an anti-IgE antibody or IgE binding fragment thereof of the present disclosure.

Suitable host cells include eukaryotic host cells, such as a mammalian cell, an insect host cell, a yeast cell; and prokaryotic cells, such as a bacterial cell. Introduction of a the nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Suitable yeast cells include, but are not limited to, *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa*, *Chlamydomonas reinhardtii*, and the like.

Suitable prokaryotic cells include, but are not limited to, any of a variety of laboratory strains of *Escherichia coli*, *Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) Science 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri*, *Shigella sonnei*, and *Shigella disenteriae*. Typically, the laboratory strain is one that is non-pathogenic. Non-limiting examples of other suitable bacteria include, but are not limited to, *Bacillus subtilis*, *Pseudomonas pudita*, *Pseudomonas aeruginosa*, *Pseudomonas mevalonii*, *Rhodobacter sphaeroides*, *Rhodobacter capsulatus*, *Rhodospirillum rubrum*, *Rhodococcus* sp., and the like. In some embodiments, the host cell is *Escherichia coli*.

Pharmaceutical Compositions

Also provided are compositions, including pharmaceutical compositions, comprising an anti-IgE antibody or IgE binding fragment thereof of the present disclosure. The pharmaceutical composition includes: an anti-IgE antibody that: specifically binds to circulating and receptor-bound IgE; does not compete for IgE binding with the antibody CIA-E-7.12 (ATCC Accession No. HB-236); and inhibits activation of cells (e.g., basophils, mast cells, eosinophils, and the like) that express the high affinity IgE receptor (FcεRI); and a pharmaceutically acceptable carrier. In certain aspects, the pharmaceutical composition of the present disclosure includes an antibody that also binds to membrane IgE (or "mIgE"), as described elsewhere herein. The pharmaceutical compositions generally include a therapeutically effective amount of the anti-IgE antibody. By "therapeutically effective amount" is meant a dosage sufficient to produce a desired result, e.g., an amount sufficient to effect beneficial or desired therapeutic (including preventative) results, such as a reduction in a symptom of an IgE-mediated disorder, as compared to a control. An effective amount can be administered in one or more administrations.

Formulations

An anti-IgE antibody of the present disclosure may be administered to the patient using any convenient means capable of resulting in the desired therapeutic effect or diagnostic effect. Thus, the anti-IgE antibody can be incorporated into a variety of formulations for therapeutic administration. More particularly, the antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, injections, inhalants and aerosols.

Formulations of the antibodies of the present disclosure suitable for administration to a patient (e.g., suitable for human administration) are generally sterile and may further be free of detectable pyrogens or other contaminants contraindicated for administration to a patient according to a selected route of administration.

In pharmaceutical dosage forms, the antibody can be administered in the form of their pharmaceutically acceptable salts, or they may also be used alone or in appropriate association, as well as in combination, with other pharmaceutically active compounds. The following methods and excipients are merely examples and are in no way limiting.

For oral preparations, the anti-IgE antibody can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The anti-IgE antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising an anti-IgE antibody or IgE binding fragment thereof of the present disclosure are prepared by mixing the antibody having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

According to one aspect, the active agent in the pharmaceutical composition is a half antibody, and the composition includes one or more components that inhibit aggregation and/or dimerization of the half antibodies. Such formulation components may be useful to maintain the antibody in a half antibody state, e.g., to prevent receptor-bound IgE cross-linking via aggregated and/or dimerized antibodies.

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration; see also Chen (1992) Drug Dev Ind Pharm 18, 1311-54.

Example antibody concentrations in a pharmaceutical composition according the present disclosure may range from about 1 mg/mL to about 200 mg/ml or from about 50 mg/mL to about 200 mg/mL, or from about 150 mg/mL to about 200 mg/mL.

An aqueous formulation of the antibody may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the antibody formulation to modulate the tonicity of the formulation. Example tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 mM.

A surfactant may also be added to the antibody formulation to reduce aggregation of the formulated antibody and/or minimize the formation of particulates in the formulation and/or reduce adsorption. Example surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Example concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, the formulation includes an anti-IgE antibody of the present disclosure, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, the formulation can be a liquid (e.g., an aqueous solution or emulsion) or lyophilized formulation thereof, suitable for parenteral administration, and can comprise: about 1 mg/mL to about 200 mg/mL of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

An anti-IgE antibody can be utilized in an aerosol formulation to be administered via inhalation. The antibody can be formulated into pressurized acceptable propellants such as dichlorodifluoromethane, propane, nitrogen and the like.

Unit dosage forms for oral administration such as syrups, elixirs, and suspensions may be provided wherein each dosage unit, for example, teaspoonful, tablespoonful, or tablet, contains a predetermined amount of the composition containing one or more inhibitors. Similarly, unit dosage forms for injection or intravenous administration may comprise the antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the antibody of interest may depend on the particular antibody employed and the effect to be achieved, and the pharmacodynamics associated with each antibody in the host.

In certain aspects, the pharmaceutical composition (optionally provided in unit dosage form) includes an anti-IgE antibody or IgE binding fragment thereof of the present disclosure present at a concentration of from about 10 mg/mL to about 1000 mg/mL, e.g., from about 25 mg/mL to about 500 mg/mL, from about 50 mg/mL to about 250 mg/mL, from about 75 mg/mL to about 200 mg/mL, or from about 100 mg/mL to about 150 mg/mL (e.g., about 125 mg/mL).

The present disclosure provides additional modes of administration, e.g., aerosol and intranasal compositions. Intranasal formulations may include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the antibody by the nasal mucosa.

An anti-IgE antibody or IgE binding fragment thereof of the present disclosure may be administered as an injectable formulation. Typically, injectable compositions are prepared as liquid solutions, suspensions, or emulsions; solid forms suitable for solution in, or suspension in, liquid vehicles prior to injection may also be prepared. The preparation may be emulsified or the antibody encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the anti-IgE antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the anti-IgE antibody or IgE binding fragment thereof is formulated in a controlled release formulation. Sustained-release preparations may be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity and possible changes in immunogenicity of antibodies comprised in sustained-release preparations may be prevented by using appropriate additives, by controlling moisture content and by developing specific polymer matrix compositions.

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms*, 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications*, 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems;

and ion-exchange-controlled gastrointestinal delivery systems, which include cationic and anionic drugs. Additional information regarding controlled release drug delivery systems may be found in Yie W. Chien, *Novel Drug Delivery Systems*, 1992 (Marcel Dekker, Inc.).

Dosages and Regimen

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. An anti-IgE antibody or IgE binding fragment thereof of the present disclosure may be administered in amounts between 1 ng/kg body weight and 20 mg/kg body weight per dose, e.g. between 0.1 mg/kg body weight to 10 mg/kg body weight, between 0.5 mg/kg body weight to 8 mg/kg body weight, between 1 mg/kg body weight to 6 mg/kg body weight, e.g. between 2 mg/kg body weight to 5 mg/kg body weight; however, doses below or above these example ranges are envisioned, especially considering the aforementioned factors. If the regimen is a continuous infusion, it can also be in the range of 1 µg to 10 mg per kilogram of body weight per minute. An anti-IgE antibody or IgE binding fragment thereof of the present disclosure may be administered as a single dose or in multiple doses. For example, an anti-IgE antibody or IgE binding fragment thereof of the present disclosure may be administered 2 times per day, 1 time per day, once every 2 days, once every 3 days, once per week, once every two weeks, once per month, once every two months, etc.

Those of skill will readily appreciate that dose levels can vary as a function of the specific antibody, the severity of the symptoms and the susceptibility of the subject to side effects. Preferred dosages for a given compound are readily determinable by those of skill in the art by a variety of means.

Routes of Administration

An anti-IgE antibody or IgE binding fragment thereof of the present disclosure is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, intraarterial, nasal, oral, and other enteral and parenteral routes of administration. Routes of administration may be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously.

The antibody may be administered to a host using any available conventional methods and routes suitable for delivery of conventional drugs, including systemic or localized routes. In general, routes of administration contemplated by the invention include, but are not necessarily limited to, parenteral, enteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

In some embodiments, a subject antibody is administered by injection, e.g., for systemic delivery (e.g., intravenous infusion) or to a local site.

The antibody may also be delivered to the subject by enteral administration. Enteral routes of administration include, but are not necessarily limited to, oral delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as an IgE-mediated disorder. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject," "individual," and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the hosts will be humans.

Methods of Treating IgE-Mediated Disorders

The present disclosure provides methods of treating a disease or disorder mediated by IgE. The methods generally involving administering to a patient in need thereof a therapeutically effective amount of an anti-IgE antibody or IgE binding fragment thereof of the present disclosure, alone (e.g., in monotherapy) or in combination (e.g., in combination therapy) with one or more additional therapeutic agents. In certain aspects, the methods include treating an IgE-mediated disorder by administering to a patient in need thereof a therapeutically effective amount of an anti-IgE antibody that specifically binds to circulating and receptor-bound IgE, that does not compete for IgE binding with the antibody CIA-E-7.12 (ATCC Accession No. HB-236), and that inhibits activation (e.g., degranulation) of cells that express the high affinity IgE receptor (FcεRI) (e.g., basophils, mast cells, eosinophils, and the like). In certain aspects, the methods of the present disclosure include administering an anti-IgE antibody that binds to circulating, receptor-bound, and membrane IgE (or "mIgE"), as described elsewhere herein.

By "treating," "treat," or "treatment" is meant alleviating or abrogating an IgE-mediated disorder and/or at least one of its attendant symptoms. As used herein, to "alleviate" a disease, disorder or condition means reducing the severity and/or occurrence frequency of the symptoms of the disease, disorder, or condition. It will be understood that references herein to "treating," "treat," or "treatment" include references to curative, palliative and prophylactic treatment.

By "IgE-mediated disorder" is meant a disorder, condition or disease which is characterized by signal transduction through an IgE receptor, including the high-affinity IgE receptor (FcεRI) and/or the low-affinity IgE receptor (FcεRII; CD23). IgE-mediated disorders include, but are not limited to those in which a type-I allergic reaction or type-I hypersensitivity is the primary event in the disease process, e.g., allergic asthma, allergic rhinitis, food allergies, allergic conjunctivitis, atopic dermatitis, anaphylaxis or anaphylactic hypersensitivity, eosinophilic esophagitis/gastroenteris, mastocytosis, bee sting reactions, drug reactions, idiopathic urticaria, angioedema, etc. IgE-mediated disorders also include those disorders in which the type-I allergic reaction or type-I hypersensitivity plays an important secondary role in the disease pathogenesis, e.g., allergic pulmonary aspergillosis, allergic purpura, hyper IgE Immune Deficiency Syndrome (HIES or Job's syndrome), rheumatoid arthritis, IgE myeloma, inflammatory bowel disease (for example, Crohn's disease, ulcerative colitis, indeterminate colitis and infectious colitis), psoriasis, bullous pemphigoid, etc.

By "therapeutically effective amount" or "efficacious amount" is meant the amount of a subject anti-IgE antibody or IgE-binding fragment thereof that, when administered to a mammal or other subject for treating an IgE-mediated disorder, is sufficient to effect such treatment for the disorder. The "therapeutically effective amount" will vary depending on the anti-IgE antibody, the disease and its severity, and the age, weight, etc., of the patient to be treated.

According to one embodiment, the methods are methods of treating a patient having asthma, e.g., allergic asthma. Asthma is a chronic inflammatory disorder of the airways causing recurrent episodes of wheezing, breathlessness, chest tightness, and/or coughing in susceptible individuals. Those skilled in the art distinguish various types of asthma, including: allergic asthma, which is thought to arise in patients having developed a hypersensitivity to environmental allergens; drug-induced asthma, typically triggered by sensitivity to aspirin or other COX inhibitors; exercise-induced asthma; near-fatal and hyperacute asthma; nocturnal asthma; occupational asthma, generally caused by exposure to certain chemicals in the workplace. Thus, asthma can be triggered by various stimuli, including airborne allergens (such as dust-mites, pollens, animal dander, fungal spores, feathers), non-specific irritants, such as tobacco smoke, chemical fumes, pollution, sulphur dioxide, and the like.

In other aspects, the methods are methods of treating a patient having allergic rhinitis. Allergic rhinitis typically involves a collection of symptoms, including inflammatory symptoms, predominantly in the nose, sinuses and eyes, which occur after exposure to airborne particles. Symptoms include sneezing; nasal obstruction; runny nose (and occasionally nosebleeds); coughing; headache; itching nose, mouth, eyes, throat, skin, or any area exposed to the allergen; impaired smell (and thus sensitivity to flavors); stuffy nose (nasal congestion); conjunctivitis; watering eyes; sore throat; and wheezing.

Allergic rhinitis may be perennial and/or seasonal. Perennial allergic rhinitis is allergic rhinitis that lasts throughout the year. It is typically caused by continuous exposure to allergens such as animal dander, indoor mould spores, or house dust mites. Seasonal allergic rhinitis is allergic rhinitis that occurs only during certain times of the year. It is commonly caused by allergies to tree, grass, and weed pollen that are produced seasonally.

According to certain embodiments, the methods are methods of treating a patient with one or more food allergies. A food allergy is an exaggerated immune response triggered by eggs, peanuts, milk, or some other specific food. Any food can cause an allergic reaction, but a few foods are the main culprits. In children, the most common food allergies are to eggs, peanuts, milk, soy, tree nuts, wheat, and shellfish (e.g., shrimp, crab, lobster, snails, clams). In older children and adults, the most common food allergies are: peanuts, tree nuts, shellfish, and fish. The symptoms may be confined mainly to the stomach and intestines, or may involve many parts of the body after the food is digested or absorbed. Symptoms may include: scratchy throat, anaphylaxis (a severe, whole-body allergic reaction that can result in death); abdominal pain; diarrhea; nausea; vomiting; stomach cramps; itching of the mouth, throat, eyes, skin, or any area; hives; angioedema (swelling, especially of the eyelids, face, lips, and tongue); light-headedness or fainting; nasal congestion; runny nose; shortness of breath; wheezing; difficulty swallowing; oral allergy syndrome. The oral allergy syndrome typically comprises itching lips, tongue, and throat, and sometimes swollen lips.

The methods of the present disclosure may be used to treat patients having other disorders in which important IgE mediated effects occur including, but not limited to, allergic pulmonary aspergillosis, allergic purpura, hyper IgE Immune Deficiency Syndrome (HIES or Job's syndrome), rheumatoid arthritis, IgE myeloma, inflammatory bowel disease (for example, Crohn's disease, ulcerative colitis, indeterminate colitis and infectious colitis), psoriasis, bullous pemphigoid, etc.

In some embodiments, an effective amount of the anti-IgE antibody is an amount that, when administered alone (e.g., in monotherapy) or in combination (e.g., in combination therapy) with one or more additional therapeutic agents, in one or more doses, is effective to reduce the symptoms of an IgE-mediated disorder (e.g., any of the IgE-mediated disorders described above, such as allergic asthma, allergic rhinitis, food allergies, etc.) in an individual by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the symptoms in the individual in the absence of treatment with the anti-IgE antibody.

Combination Therapy

In some embodiments, a subject method of treating an IgE-mediated disorder includes administering: an anti-IgE antibody or IgE binding fragment thereof of the present disclosure; and one or more additional therapeutic agents. Suitable additional therapeutic agents include, but are not limited to, an additional anti-IgE antibody (e.g., an additional antibody provided by the present disclosure, omalizumab, lumiliximab, and/or the antibody CIA-E-7.12 (ATCC Accession No. HB-236)), immunosuppressive agents, anti-inflammatory agents, and the like. The treatment methods may include administration of the anti-IgE antibody or IgE binding fragment thereof co-administered or co-formulated with a second medication/drug selected from the group consisting of steroids, including corticosteroids (inhaled, oral); bronchodilators (such as long-acting beta-2 agonists; short-acting beta-2 agonists); other anti-IgE agents, such as an IgE vaccine; leukotriene antagonists/inhibitors; methylxanthines; antibodies directed against interleukins involved in airway inflammation, e.g. monoclonal antibodies directed against IL-4 or IL-13 or TNF; cromolyns, such as cromolyn sodium; nedocromil sodium; anticholerginics and PDE inhibitors.

Administration "in combination with" one or more further therapeutic agents includes simultaneous (concurrent) and consecutive administration in any order.

Patients Suitable for Treatment

A variety of patients are suitable for treatment with the methods of the present disclosure. Suitable patients include any individual, e.g., a human, suffering from an IgE-mediated disorder including, but not limited to a disorder in which a type-I allergic reaction or type-I hypersensitivity is the primary event in the disease process, e.g., allergic asthma, allergic rhinitis, food allergies, allergic conjunctivitis, atopic dermatitis, anaphylaxis or anaphylactic hypersensitivity, eosinophilic esophagitis/gastroenteris, mastocytosis, bee sting reactions, drug reactions, idiopathic urticaria, angioedema, etc. Suitable patients also include any individual, e.g., a human, suffering from an IgE-mediated disorder in which the type-I allergic reaction or type-I hypersensitivity plays an important secondary role in the disease pathogenesis, e.g., allergic pulmonary aspergillosis, allergic purpura, hyper IgE Immune Deficiency Syndrome (HIES or Job's syndrome), rheumatoid arthritis, IgE myeloma, inflammatory bowel disease (for example, Crohn's disease, ulcerative colitis, indeterminate colitis and infectious colitis), psoriasis, bullous pemphigoid, etc. Those in need of treatment include those already with the condition or disorder, as well as those susceptible to having the condition or disorder, or those in which the condition or disorder is to be prevented. An individual susceptible to having an IgE-mediated disorder may be identified by determining total and/or allergen-specific IgE, allergen skin test, clinical and/or family history, etc.

Kits

The present disclosure provides kits (e.g., therapeutic kits) that include an anti-IgE antibody or IgE binding fragment thereof of the present disclosure. Such kits are useful, e.g., in carrying out the methods of the present disclosure.

The kit may include one or more of: an anti-IgE antibody or IgE binding fragment thereof of the present disclosure, a nucleic acid encoding the same, or a cell comprising the nucleic acid encoding the same. The anti-IgE antibody in a kit of the present disclosure may be humanized. Kits of the present disclosure may include the anti-IgE antibody present in a pharmaceutical composition, e.g., in a single dose, two or more unit dosages, etc.

In addition to above-mentioned components, the kit may include instructions for using the components of the kit, e.g. to practice the treatment method of the present disclosure. The instructions for using the components of the kit are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. compact disc-read only memory (CD-ROM), digital versatile disk (DVD), flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Commercially available reagents referred to in the Examples were used according to manufacturer's instructions unless otherwise indicated. Unless otherwise defined, all technical and scientific terms used herein have the same meaning as commonly understood by one of ordinary skill in the art to which this invention belongs. Example methods and materials are described below although methods and materials similar or equivalent to those described herein can also be used in the practice or testing of the present invention. The materials, methods, and examples are illustrative only and not intended to be limiting in scope.

Example 1

Generation and Purification of Monoclonal Anti-Human IgE Antibody P6.2

Hybridoma P6.2 was produced by injection of human FcεRIa transgenic mice with bone marrow derived mast cells sensitized with human IgE (IgE, λ). The immunized spleen cells were fused with SP 2/0 cells and screened for binding to a human IgE (IgE, κ). The hybridoma cells were selected with HAT medium. mAb P6.2 producing cells were grown in the culture medium and the antibodies were purified by protein L affinity chromatography.

mAb P6.2 is a low affinity (Kd=$2.54 \times 10^{-6}$ M) mouse anti-human IgE monoclonal antibody (IgG1, κ) that recognizes a conformational epitope in the CHε2-CHε4 region, as binding is lost when IgE is denatured. P6.2 is capable of binding to both soluble (serum) IgE and IgE bound to FcεRIs as its IgE binding site does not overlap with the IgE-FcεRI binding site.

The variable heavy ($V_H$) and light ($V_L$) chain sequences, and the nucleotide sequences encoding the same, are shown in FIG. 1. The $V_H$ and $V_L$ CDR sequences are underlined.

Example 2

Figure 3:
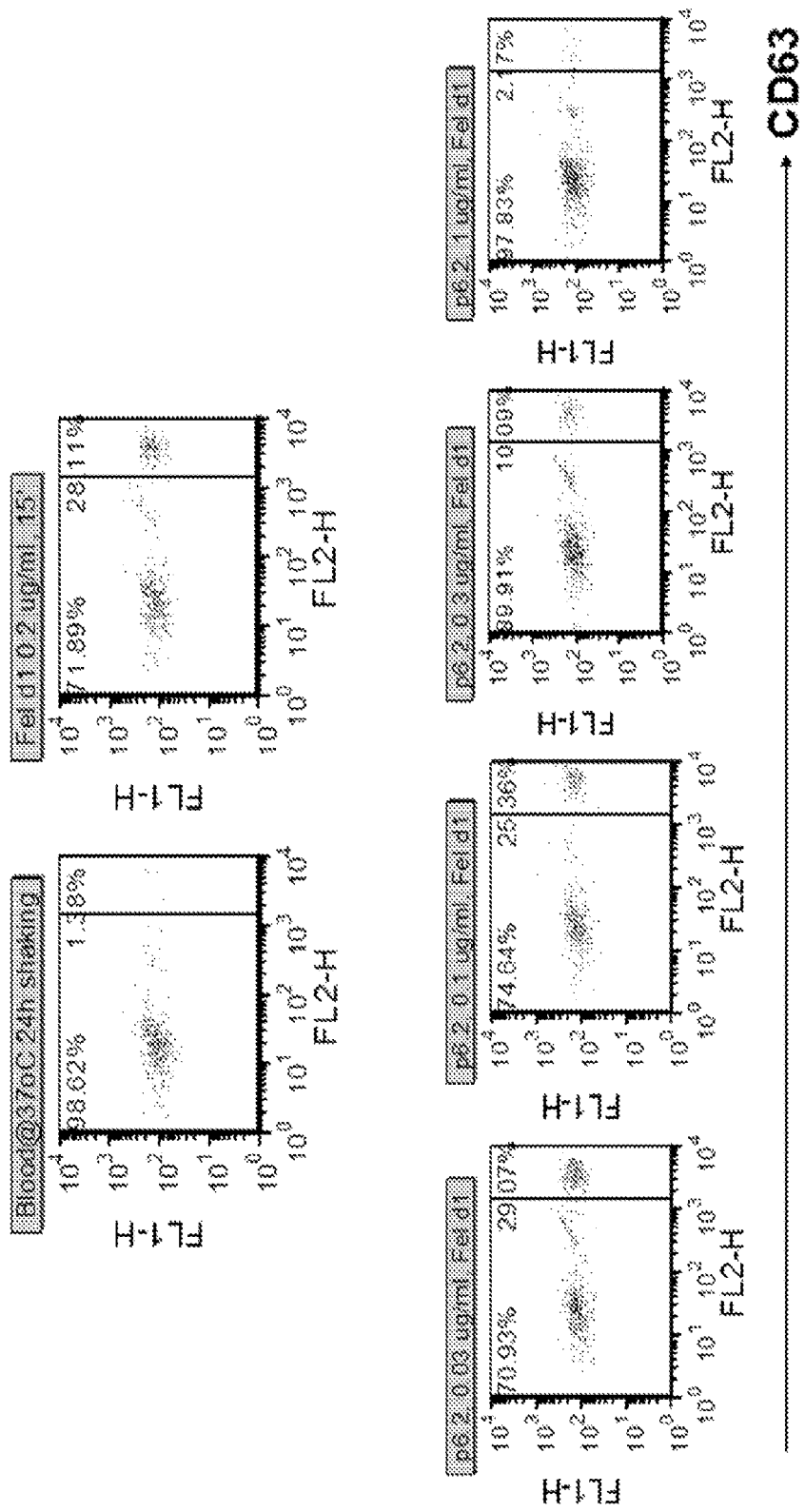
FIG. 3 shows flow cytometry data obtained from a basophil activation (BAT) assay, indicating that an example antibody according to one embodiment of the present disclosure suppresses allergen-induced basophil activation in a dose range as low as from 0.03 to 1 µg/ml.

Antibody P6.2 does not Induce Basophil Activation at Concentrations as High as 40 μg/mL A Basophil Activation Test (BAT) assay was performed to determine the ability of antibody p6.2 and anti-IgE antibody CIA-E-7.12 (ATCC Accession No. HB-236)("E-7.12") to induce basophil activation at various concentrations. Blood (100 μl) from cat or peanut allergic subjects were incubated with varying amounts of purified mAb p6.2 (1-40 μg/ml range) for 20 minutes at 37° C. to test whether this antibody activates basophils. The activation reaction was stopped by EDTA and the cells were then stained for 20 minutes on ice with a cocktail of CD123-FITC/CD63-PE/HLA-Dr-PerCP. Followed by lysis of red blood cells, the stained cells were analyzed with flow cytometry. The basophil population was gated in the CD123 positive/HLA-Dr negative population. CD63 expression in this basophil population was calculated and analyzed. For determination of whether mAb p6.2 would block allergen triggered basophil activation, the blood samples were incubated with mAb p6.2 for 24 hours and/or 48 hours at 37° C. with constant shaking, then cat allergen Fel d1 (0.02-0.2 µg/ml) or peanut allergen (Ara h1, 2 and 6 combined, 0.1-1.0 µg/ml) were added into the blood for 15 minute incubation at 37° C. to activate the basophils. BAT results are shown in FIGS. 2 and 3.

Anti-IgE antibodies typically crosslink surface-bound IgE molecules, in turn crosslinking the FcεRI molecules on human basophils/mast cells to initiate acute allergic reactivity. As shown in FIG. 2, however, mAb p6.2, although capable of binding to the cytophilic IgE on the cell surface, showed little ability to activate basophils at concentrations as high as 40 µg/ml. In the basophil activation test (BAT), the purified mAb p6.2 does not increase CD63 expression, a marker for basophil activation, across a dose range from 5 to 40 µg/mL, whereas anti-IgE Ab E-7.12 (1 µg/ml) induced CD63 expression.

Example 3

Antibody P6.2 Suppresses Cat Allergen Fel D1-Induced Basophil Activation

A Basophil Activation Test (BAT) assay was performed as described above to determine the ability of antibody P6.2 to suppress cat allergen Fel d1-induced basophil activation. As shown in FIG. 3, cat allergen Fel d1-induced CD63 expression of blood basophils from cat allergic subjects was significantly suppressed by pre-incubation of blood with mAb p6.2 (0.03 µg/ml-1 µg/ml range) for 24 hours in a dose dependent manner, with the strongest inhibition effect at 1 µg/ml.

Figure 4:
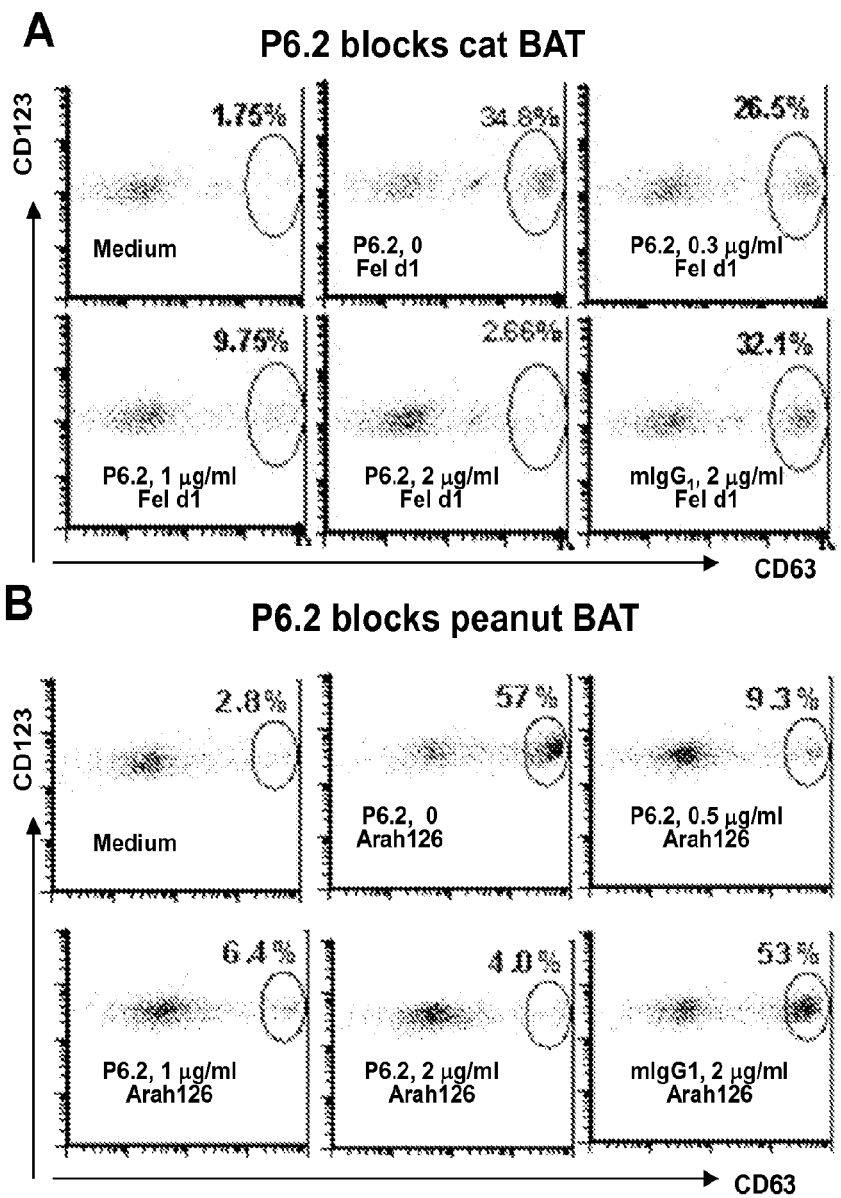
FIG. 4 shows additional BAT assay data demonstrating that P6.2 blocks cat (A) and peanut (B) allergen mediated basophil activation. Mouse IgG1 was used as an isotype control for P6.2.

The results of additional basophil activation tests (BAT) further demonstrating that P6.2 blocks cat and peanut allergen-induced basophil activation are shown in FIG. 4. Cat allergen (Fel d1) induced basophil activation as measured by CD63 expression on allergic subjects' blood basophils was strongly blocked in a dose dependent manner by 48 hour pre-treatment with P6.2 at 0.3 µg-2 µg/ml with over 90% inhibition at 2 µg/ml (FIG. 4, Panel A, middle panel on second row). Peanut allergen (Ara h1, h2 and h6) induced basophil activation was also almost completely blocked by P6.2 at 2 µg/ml (FIG. 4, Panel B, right panel) in a P6.2 dose-dependent manner (data not shown). These data show that low doses of P6.2 effectively block allergen driven human basophil activation.

Example 4

Antibody P6.2 Blocks Peanut and Cat IgE-Mediated PCA

Passive Cutaneous Anaphylaxis (PCA) assays were performed to investigate the ability of mAb p6.2 to block peanut and cat allergic IgE-mediated PCA. The back skin of hFcεRIα Tg mice was intradermally injected with IgE (8-10 spots per mouse skin), purified from peanut allergic patient's plasma for local sensitization for overnight to four days. To test whether mAb p6.2 would activate mast cells, the sensitized spots were got a local injection of various amounts of mAb p6.2 (1-100 µg/ml range), with PBS negative control; and polyclonal rabbit anti-human IgE (0.1-1 µg/ml) as the positive control. Ten minutes later, 200 µl of 1% Evan's blue dye was intravenously injected to assess the local allergic reactivity. To test whether mAb p6.2 would block allergen-mediated PCA, the series diluted peanut specific IgE (2 µg/ml-0.125 µg/ml) were sensitized the hFcεRIα Tg mice for hours, followed by 50 µg (equivalent to 2 mg/kg body weight) mAb p6.2 injection intraperitoneally, with 50 µg of mouse IgG1 as control. Four days later, peanut allergy Ara h2 (10 µg) was injected intravenously and the blue spot development was measured 30 minutes post-intravenous dye injection.

Figure 5:
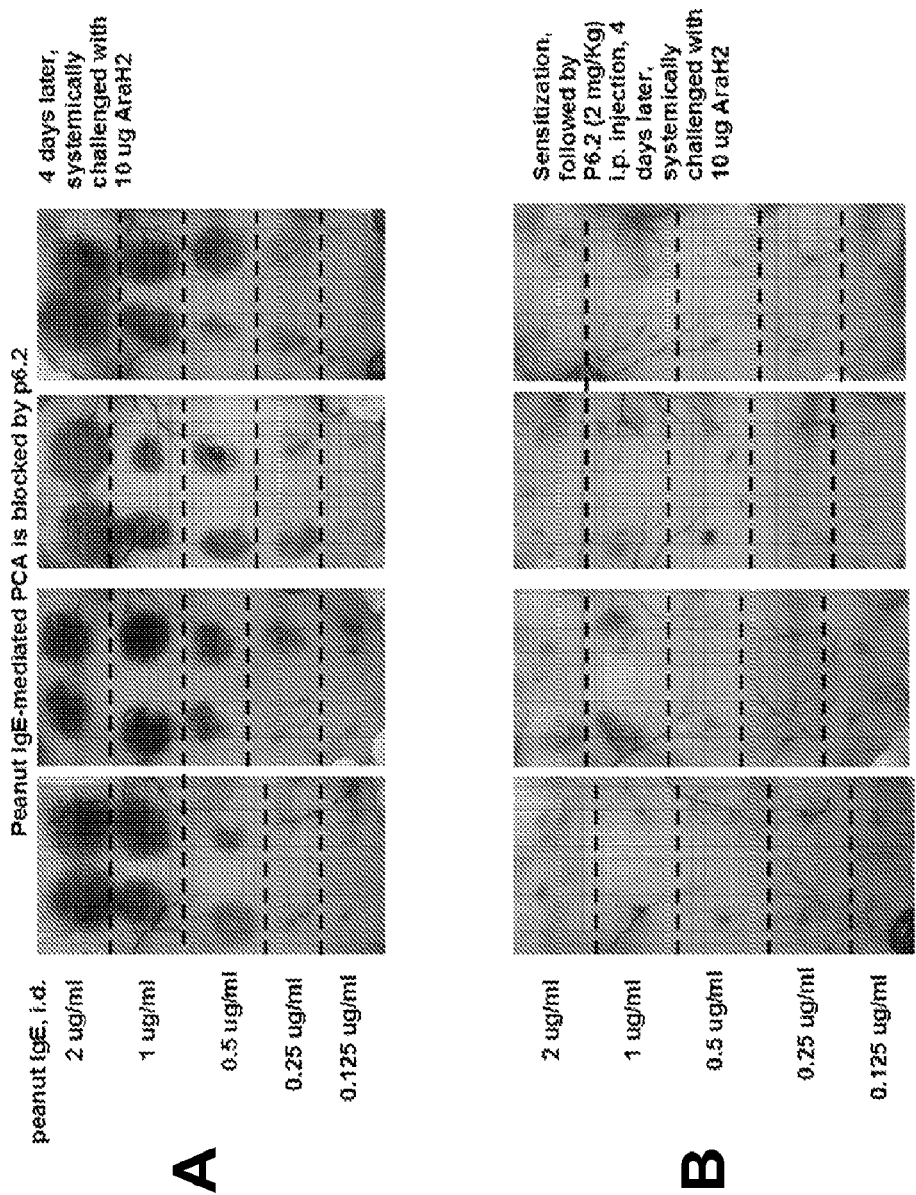
FIG. 5 shows the results of a Passive Cutaneous Anaphylaxis (PCA) assay, indicating that allergen-induced IgE-mediated PCA occurs in the absence of antibody (Panel A) while an example antibody according to one embodiment of the present disclosure blocks allergen-induced IgE-mediated PCA (Panel B).

Peanut IgE-mediated PCA reactions upon Ara h2 challenge are shown in FIG. 5 (Panel A)(N=4). A peanut IgE dose-dependent PCA reaction was observed, with a strong PCA reaction at the IgE sensitization concentration of 1 to 2 µg/ml, and weak or moderate PCA at 0.25 µg/ml to 0.5 µg/ml. The PCA reaction was almost completely blocked in the mice given mAb p6.2 intraperitoneally at 2 µg per gram body weight (equivalent to the dose of 2 mg/kg body weight)(FIG. 5, Panel B; N=4).

Figure 6:
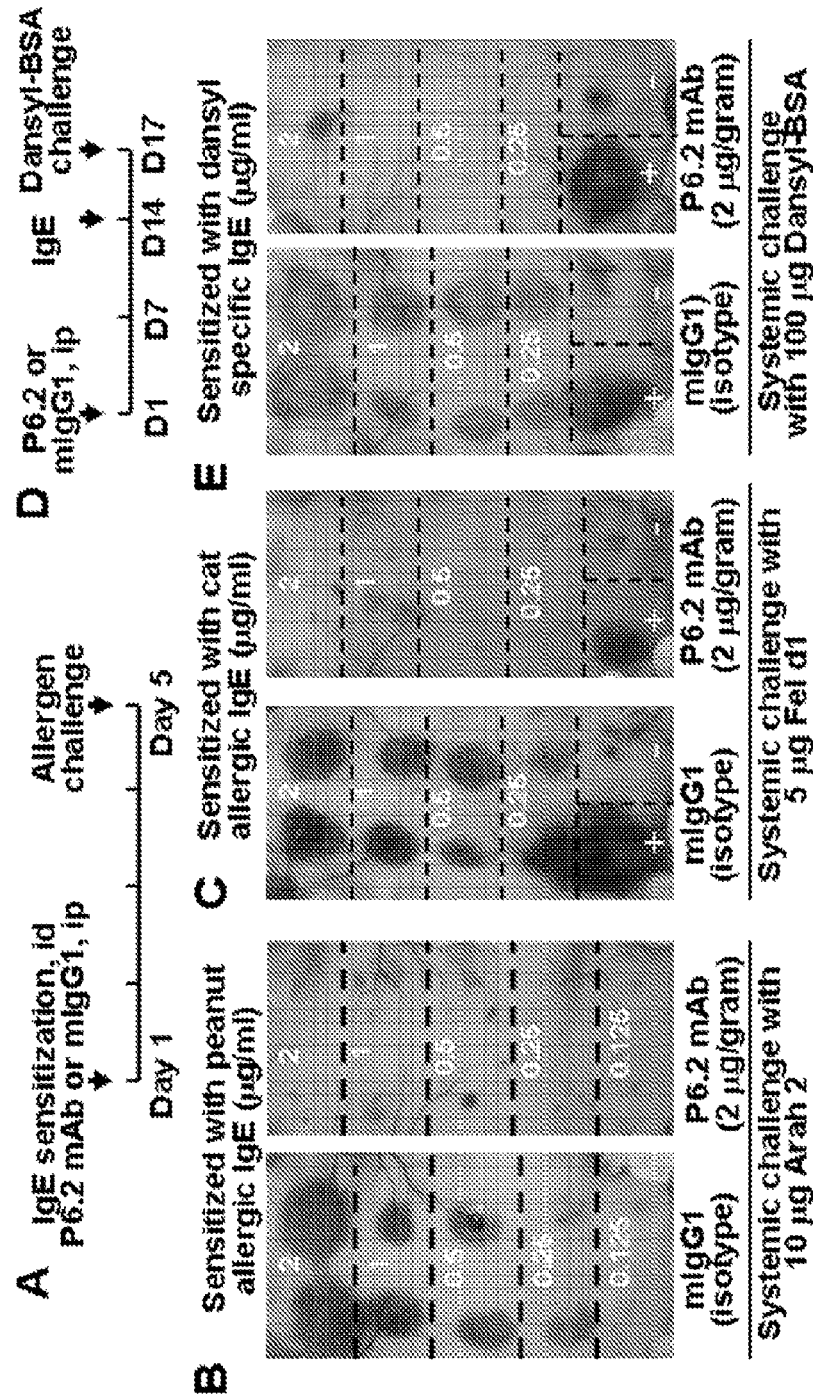
FIG. 6 shows additional PCA assay data demonstrating that P6.2 blocks PCA reactivity. The ability of P6.2 to block PCA is shown for peanut (B), cat (C) and dansyl (D & E) specific IgE. Mouse IgG1 (mIgG1) was used as an isotype control. The positive control (+) for hFcεRI mediated release was local injection of 1 µg of polyclonal anti-human IgE, whereas the negative control (−) was local PBS injection.

The results of additional PCA assays demonstrating that P6.2 blocks peanut and cat allergic IgE-mediated PCA are shown in FIG. 6. In vivo therapeutic effects of P6.2 mAb on allergic reactivity were demonstrated using PCA in hFcεRIα transgenic mice. As shown in FIG. 6, hFcεRIα mice were skin-sensitized with a serially diluted peanut, cat or dansyl-specific IgE (2-0.125 µg/ml), treated with P6.2 or mIgG1 as an isotype control, and then challenged with corresponding allergens as indicated. P6.2 at 2 µg/gram body weight when given with the schedule shown in FIG. 6, Panels A or D, almost completely blocked the peanut allergic IgE- (FIG. 6B), cat allergic IgE- (FIG. 6, Panel C), and dansyl specific IgE- (FIG. 6, Panel E) mediated PCA reactivity (N=4 for each group). This inhibition of allergic reactivity by P6.2 persisted out to 17 days as shown for dansyl specific IgE-mediated PCA (FIG. 6, Panels D, E), and for peanut allergic IgE-mediated PCA (data not shown), indicating that P6.2 has a relatively prolonged effect.

Example 5

Antibody P6.2 Decreases Basophil and Mast Cell Surface IgE Levels

Figure 7:
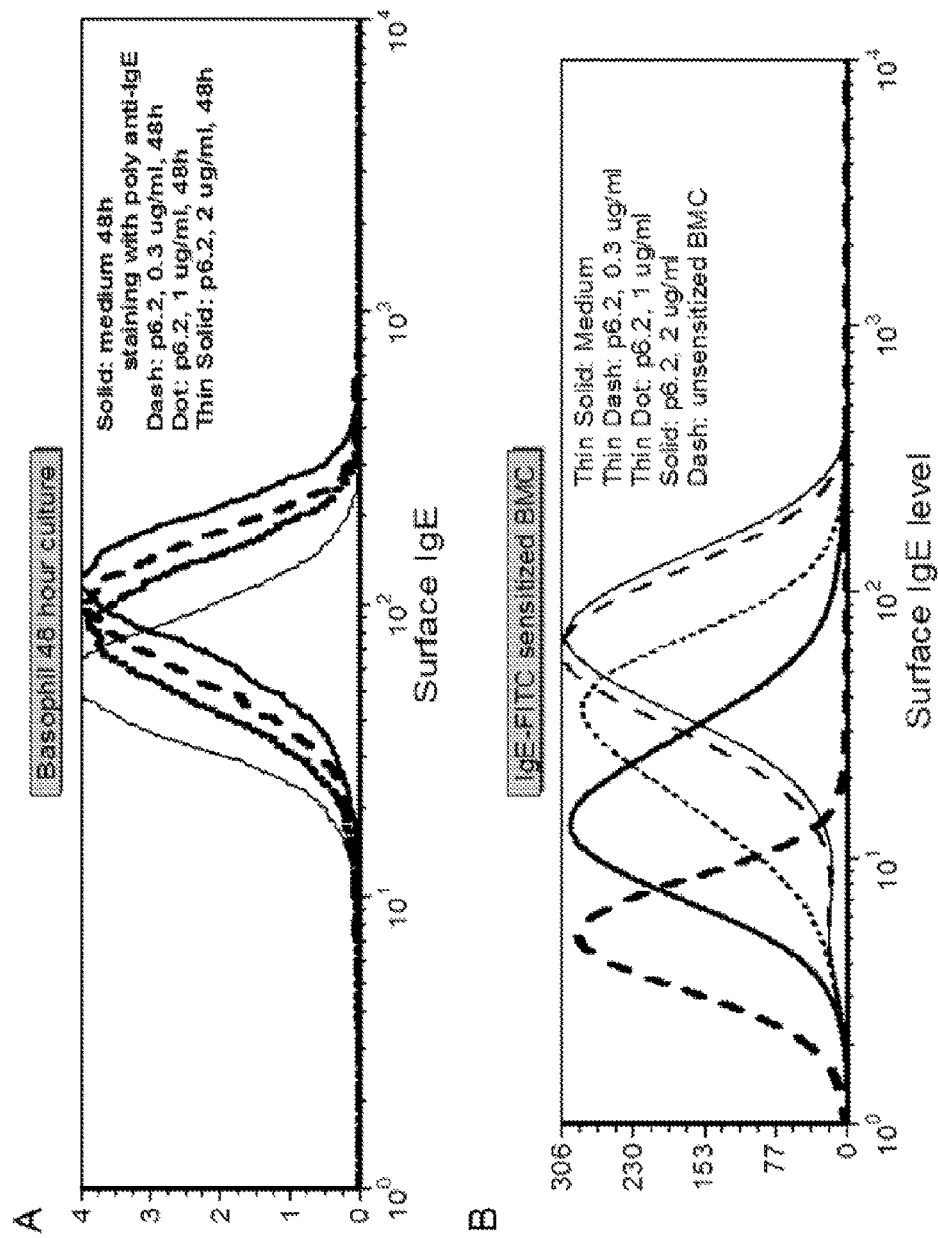
FIG. 7 shows flow cytometry data indicating that treatment of basophils (Panel A) and mast cells (Panel B) with an example antibody according to one embodiment of the present disclosure reduces the amount of IgE bound to the surface of the treated cells.

To investigate whether antibody P6.2 is capable of reducing the amount of IgE bound to the surface of basophils, blood samples were incubated with mAb P6.2 for 24-48 hours at room temperature with constant shaking, followed by staining with rabbit anti-human IgE-FITC/CD123-PE/HLA-Dr-PerCP for 20 min on ice with shaking. The surface IgE expression levels were determined by flow cytometry analysis. As shown in FIG. 7, Panel A, surface IgE on basophils was decreased by the treatment of mAb P6.2 in a dose-dependent manner, with the strongest decreasing effect at 2 µg/ml.

To investigate whether antibody P6.2 is capable of reducing the amount of IgE bound to the surface of mast cells, bone marrow cells of human FcεRIα transgenic mice were cultured in the presence of mouse IL-3 to generate BMMC by culturing with 10% FBS DMEM supplemented with the recombinant mouse IL-3 (10 ng/ml) for 6 weeks. The BMMC (with human FcεRIα surface expression and mouse c-kit (CD117) expression as indicator) reached ~60% in 4 weeks, ~80% in 5 weeks and >90% in 6 weeks. Sensitization of the differentiated BMMC with human IgE demonstrated that the expressed FcεRIα on BMMC is functional, as they were able to bind to human IgE labeled with FITC.

To test the effect of P6.2 on surface IgE level, the FITC labeled human IgE was use to sensitized the BMMC for 2 hour at 37° C. with agitation, followed by incubation with various amount of P6.2 for 48 hours at 37° C. with constant shaking (130 RPM). The cultured cells were then stained with PE-labeled anti-human FceRIa antibody and PerCP-labeled anti-mouse c-kit antibody, followed by flow cytometry analysis.

BMMC were sensitized with FITC labeled human IgE, followed by incubation with various amount of P6.2 for 48 hours. The surface IgE expression on the BMMC was measured with flow cytometry. As shown in FIG. 7, Panel B, surface IgE on the BMMC decreased by the treatment of mAb P6.2 in a dose-dependent manner, with the strongest decreasing effect at 2 μg/ml.

Example 6

Antibody P6.2 does not Compete with Antibody E-7.12 for Binding to IgE

Figure 8:
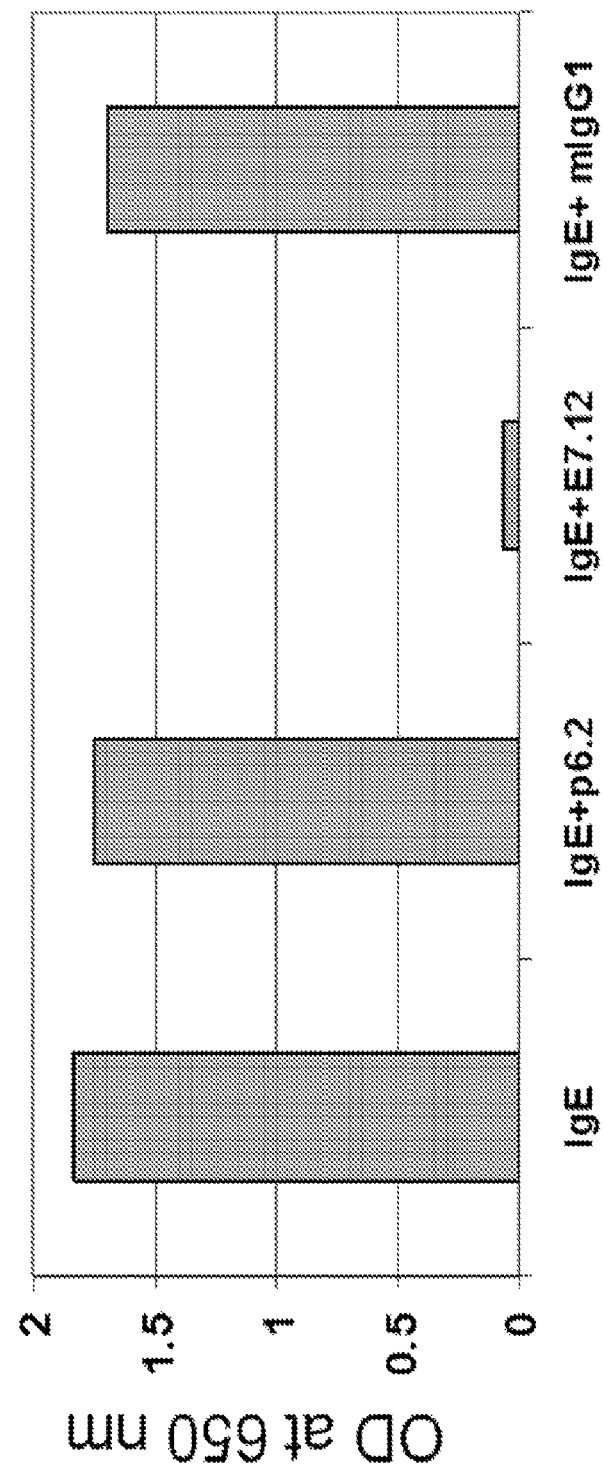
FIG. 8 depicts results from a competitive binding assay showing that antibodies P6.2 and E7.12 do not compete for binding to IgE.

Competitive ELISA was used to evaluate whether mAb P6.2 competes with antibody CIA-E-7.12 (ATCC Accession No. HB-236)("E-7.12") for IgE binding. An ELISA plate was coated with anti-human IgE mAb E4.15 (2 μg/ml) as a capture antibody. Standard IgE (100 ng/ml) was pre-incubated with medium, P6.2 (2 μg/ml), E7.12 (1 μg/ml) and mouse IgG1 (2 μg/ml) for 1 hour prior to addition to the ELISA plate. After a 2 hour incubation, the reaction was washed and incubated with AP-labeled polyclonal anti-human IgE, followed by color development with blue phosphate substrates. As shown in FIG. 8, antibody E7.12 blocks the IgE binding to the coated plate, whereas P6.2 mAb and control mouse IgG1 do not, indicating that mAb P6.2 and antibody E7.12 bind to different epitopes of IgE.

Example 7

Antibody P6.2 Provides Protection from Systemic Allergic Reactivity

Figure 9:
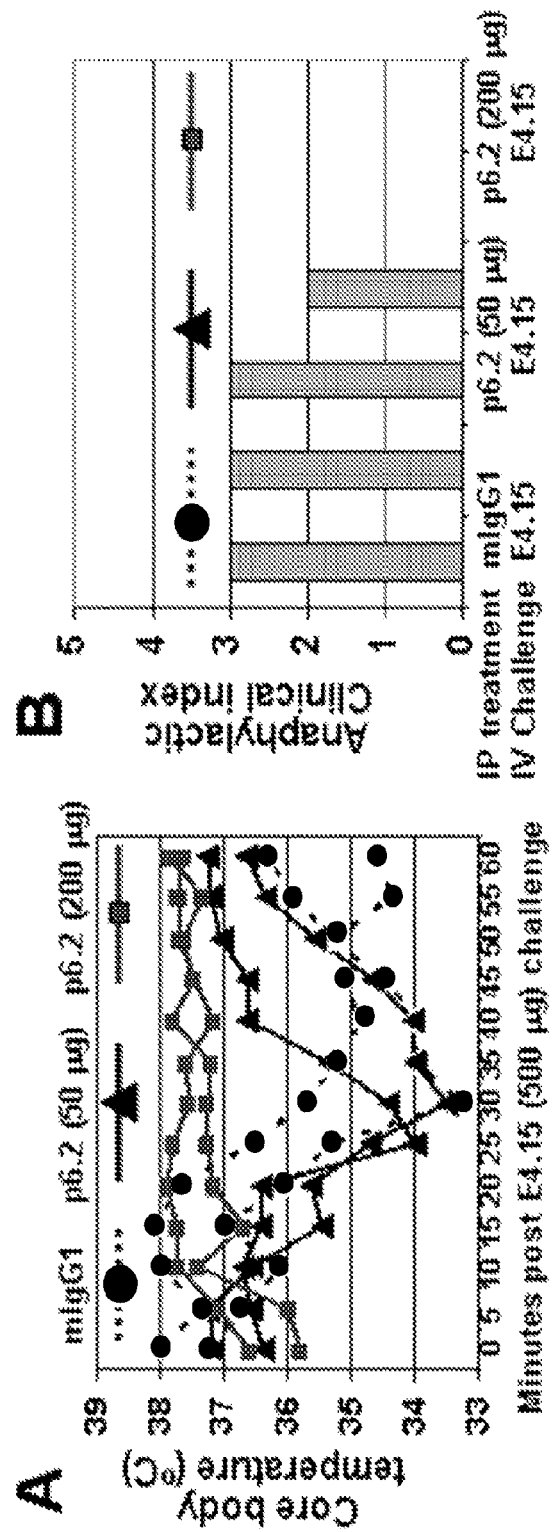
FIG. 9 shows data indicating that P6.2 pre-treatment renders protects IgE sensitized hFcεRIα Tg mice from systemic reactivity. Panel A, Core body temperature drop was seen in control (0) and 50 µg p6.2 (Δ) treated mice but not in those given 200 µg P6.2 (□). Panel B, Anaphylaxis clinical index in the three groups of mice.

To test whether p6.2 was able to provide systemic protection from allergen reactivity, hFcεRIα Tg mice systemically sensitized by passive administration of human IgE were treated i.p. with P6.2 (50 and 200 μg/per mouse, respectively) or 200 μg/mouse of control mouse IgG1. No signs of allergic reactivity (triggering allergic cell release) were observed in the first hour post P6.2 injection (data not shown). Two days later, all mice were challenged i.v. with 500 μg of mAb anti-IgE E4.15 and core body temperatures and the systemic anaphylactic clinical index recorded. As shown in FIG. 9, clear systemic reactivity was induced by anti-IgE E4.15 in sensitized mice pretreated with the isotype control or 50 μg P6.2 but not in the mice pretreated with 200 μg of P6.2.

Example 8

Figure 10:
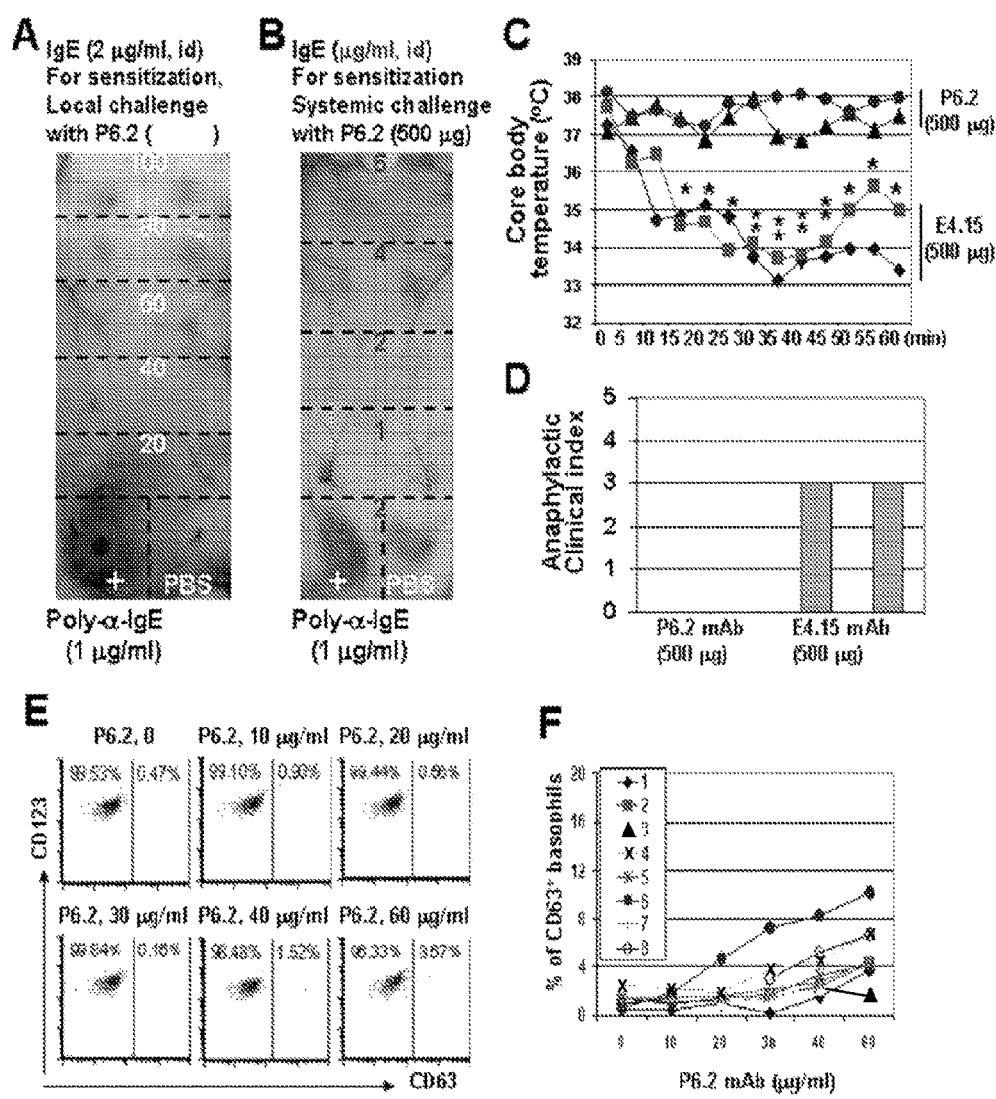
FIG. 10 provides data demonstrating the inability of P6.2 per se to induce allergic and anaphylactic reaction. * for p<0.05 and ** for p<0.01 in (C) with Student t test.

Antibody P6.2 does not Itself Induce Anaphylactic Degranulation at Levels that Markedly Block Allergic Reactivity Binding of an anti-IgE antibody to IgE bound to FcεRI on the surface of allergic effector cells generally leads to FcεRI crosslinking and induction of degranulation/allergic reactivity. Thus, it was critical to document the failure of P6.2 per se to induce this allergic activity. To test this, we've employed multiple experimental systems/assays to rigorously evaluate the ability of P6.2 to trigger allergic reactions and thereby define its in vitro safety profile. The results of these experiments are summarized in FIG. 10. For PCA, the hFcεRIα Tg mice were sensitized intradermally (id) with various concentrations of myeloma IgE (2 μg/ml for FIG. 10, Panel A; 1-6 μg/ml for FIG. 10, Panel B). This was followed by challenges with increasing amounts of P6.2 either locally (doses shown in yellow in FIG. 10, Panel A) or systemically (500 μg, FIG. 10, Panel B). On local challenge, P6.2 showed no PCA reactivity at doses up to 60 μg/ml and then weak reactivity at doses of 80-100 μg/ml (FIG. 10, Panel A). The positive control, 1 μg/ml of polyclonal rabbit anti-IgE, induced strong PCA reactivity (lower right corner, FIG. 10, Panel A). Systemic challenge with 500 μg P6.2 did not trigger PCA reactivity (FIG. 10, Panel B).

To test whether P6.2 would induce in vivo systemic anaphylaxis, hFcεRIα Tg mice systemically sensitized with IgE were challenged with 500 μg of P6.2, or anti-human IgE mAb E4.15 (ATCC HB235) (32) as a positive control. A fall in core body temperature, a sensitive indicator of systemic anaphylaxis in mice (33), was seen in the mice challenged with E4.15 but not in those challenged with mAb P6.2 (FIG. 10, Panel C). Correspondingly, a positive anaphylactic clinical score was only observed in E4.15, but not in P6.2, challenged mice (FIG. 10, Panel D).

In vitro using whole human blood, P6.2 did not increase basophil CD63 expression at doses of 10-40 μg/mL in seven of eight donors tested (FIG. 10, Panels E & F) in the BAT. However, the highest doses of P6.2 tested (40-60 μg/ml) induced weak CD63 expression in one donor (Donor 6 in FIG. 10, Panel F). Overall, these data indicate that P6.2 does not show basophil allergic activation at doses <40 μg/ml.

Example 9

Antibody P6.2 Down-Regulates Basophil Surface FcεRI Expression

Figure 11:
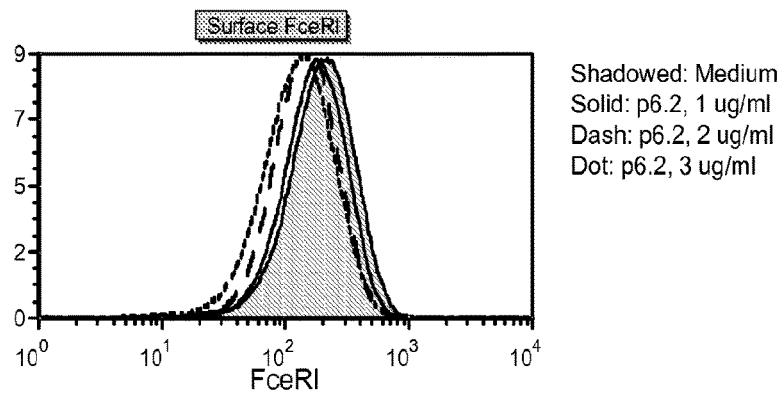
FIG. 11 provides data demonstrating that P6.2 down-regulates surface FcεRI expression on basophils, representative of 4 experiments.

To define potential mechanisms responsible for the beneficial effects of P6.2, we assessed the level of surface FcεRI expression on basophils following the P6.2 treatment. PBMC or whole blood cells were incubated with medium or various amounts of P6.2 (1 μg/ml-3 μg/ml ranges) for 5 days, followed by FACS analysis. FIG. 11 is one representative experiment showing that the basophil expression of FcεRI but not that of CD123 (IL-3Ra) was decreased by treatment of P6.2 in a dose dependent manner (FIG. 11, upper vs lower panel).

Example 10

Antibody P6.2 Down-Regulates Mast Cell Surface IgE and FcεRI

Figure 12:
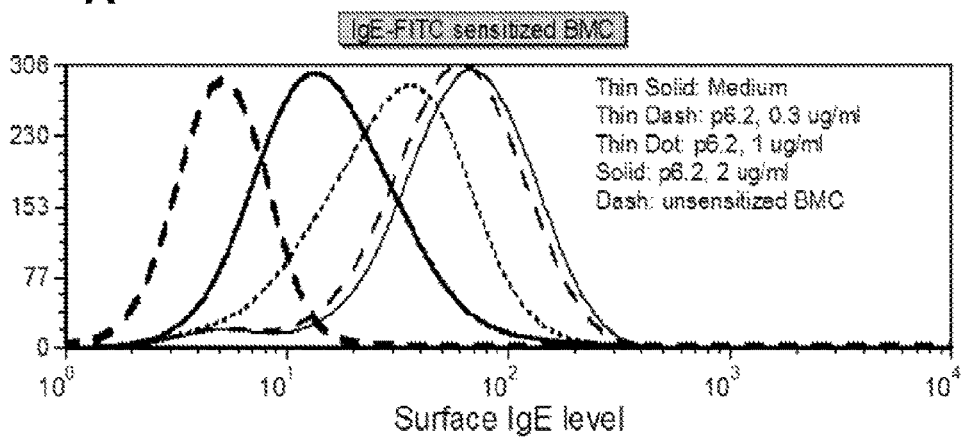
FIG. 12 shows data indicating that P6.2 down-regulates the surface IgE and FcεRI expression on mast cells including in the presence of free IgE. Data is representative of 3 experiments.

To define the effects of P6.2 on mast cell surface IgE and FcεRI expression, bone marrow-derived mast cells (BM-MCs) from hFcεRIα Tg mice were sensitized with FITC-labeled human IgE, incubated with P6.2, and then assessed for mast cell surface level of FITC-IgE and the hFcεRIα. Mouse C-kit served as an internal staining control. As shown in FIG. 12, after 5 day culture with P6.2, surface FITC-IgE levels were markedly decreased in a P6.2 dose-dependent manner (FIG. 12, Panel A). Simultaneous examination of surface FITC-IgE and FcεRIα levels revealed that surface IgE and FcεRI levels were differentially down-regulated, with the IgE level being more profoundly affected (FIG. 12, Panel B) with no effect on C-kit as expected. These results suggest that, not unexpectedly, surface FcεRI levels are being partially reconstituted either by newly synthesized FcεRIs or by recycling of internalized FcεRIs back to the surface of the cultured BMMCs.

To examine whether P6.2 was able to down-regulate the surface IgE and FcεRI expression on BMMCs in the presence of free IgE, conditions mimicking the clinical situation in humans where free IgE is present in the circulation, BMMCs sensitized with FITC-IgE were supplemented with un-labeled IgE in the culture medium, followed by addition of P6.2 for 5 day culture prior to FACS analysis. As shown in FIG. 12, Panel C, down-regulation of the surface IgE levels were clearly observed while change albeit less in FcεRI was seen indicating that P6.2 remains functional in the presence of free IgE. In vivo, this weak interaction between free IgE and P6.2 is expected serving to maintain P6.2 in the circulation while allowing it to dissociate and interact with IgE on basophils and mast cells.

To directly test whether P6.2 that is already bound to IgE would later dissociate and become active drug, we pre-incubated the P6.2 with IgE for 60 minutes. The resulting P6.2-IgE complexes were added with FITC-IgE sensitized BMMCs for 5 day culture. The data presented in FIG. 12, Panel C demonstrates that the IgE down-regulation affected by P6.2 in the complex was not substantially different from that seen when P6.2 was added directly. These data indicate that P6.2's binding to free IgE is not "neutralized" but, given P6.2's low affinity, remains available as active drug upon subsequent dissociation from the complex.

Example 11

Antibody P6.2 Directly Mediates Internalization of Surface IgE

To document and understand how surface IgE/FcεRI is down-regulated by P6.2, we employed confocal microscopy to define whether P6.2 drives the internalization of surface IgE/FcεRI complexes. FITC-IgE sensitized BMMCs were treated with a) 2 µg/ml of p6.2 for 24 and 48 hours, b) mouse IgG1 as the isotype control or c) polyclonal anti-IgE antibody as the positive control. In untreated and mouse IgG1 controls, IgE (FITC labeled) remained stably bound on the surface at 24 (not shown) and 48 hours; being detected as bright rings on the periphery of BMMCs with minimal internalization (minimal dots inside the cells in the overlay, FIG. 13, Panel A). The bright surface rings became markedly dimmer in BMMCs treated with P6.2 for 48 hours; instead, numerous fine dots appeared inside the cells in the overlay view (middle panel of the FIG. 13, Panel A). Confocal sections from the top to bottom of the P6.2 treated BMMCs demonstrated that the fine dots were located intracellularly, being distributed throughout all the sections (FIG. 13, Panel B, enlarged from the outlined area of the middle panel of FIG. 13, Panel A). These data clearly show that surface IgE has undergone internalization triggered by P6.2 treatment. This P6.2 induced internalization of surface IgE exhibited a striking distinct pattern compared with that triggered by polyclonal anti-IgE. In the latter case polarized distribution of surface IgE with large aggregates and capping was seen (Right panel, FIG. 13, Panel A). These data confirm the concept that P6.2 induces this distinctive form of internalization as its mechanism to rapidly down-regulate surface IgE/FcεRI.

Example 12

Figure 14:
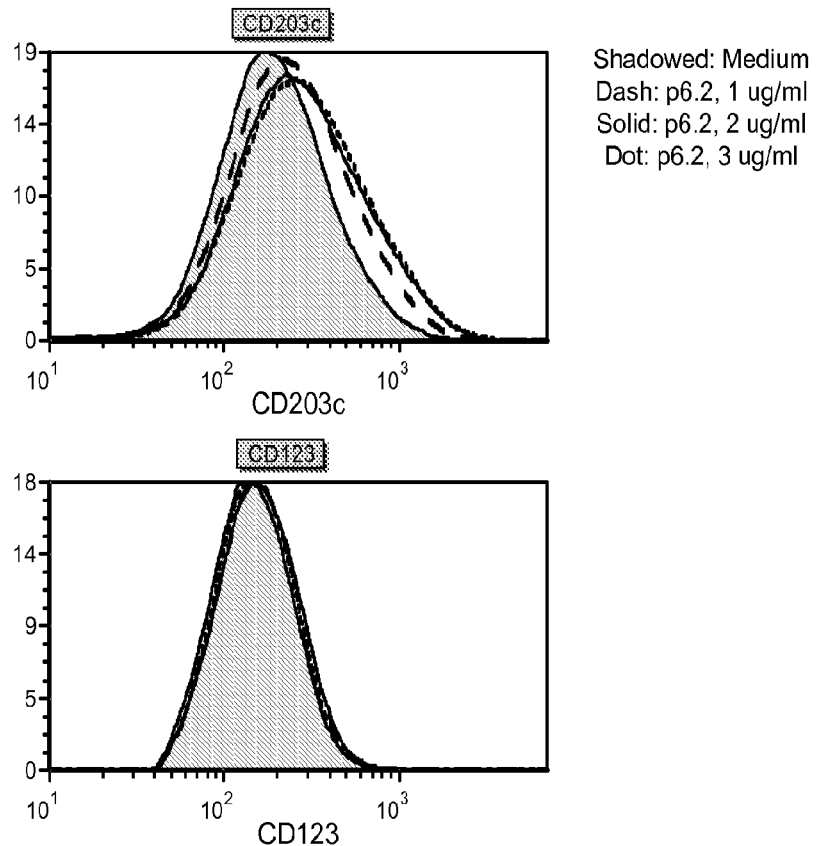
FIG. 14 shows data demonstrating that low doses of P6.2 up-regulate basophil surface CD203c expression.

Antibody P6.2 Leads to Low-Level Activation of the Piecemeal Degranulation Pathway While therapeutic concentrations of P6.2 did not activate the anaphylactic degranulation pathway, e.g., CD63 expression, they did weakly activate the piecemeal degranulation pathway as evidence by increased CD203c expression. FIG. 14 is the representative data showing that P6.2 at 1-3 µg/ml was able to induce a small but reproducible up-regulation of CD203c, a marker of piecemeal degranulation on basophils. As piecemeal degranulation is associated with allergic desensitization but not anaphylactic degranulation, activation of this piecemeal degranulation pathway may well be another important mechanism responsible for the P6.2 mediated therapeutic effects via relatively rapid induction of effector cell desensitization.

Example 13

Figure 15:
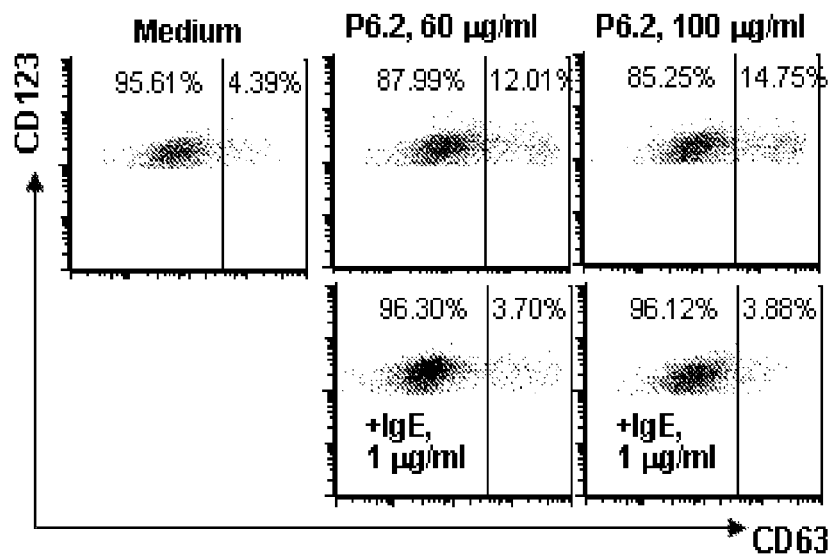
FIG. 15 provides BAT assay data indicating that basophil activation mediated by high doses of P6.2 (top panels, center and right) did not occur in the presence of soluble IgE (bottom two panels).

Protection of Basophil Activation Mediated by High Doses of Antibody P6.2 in the Presence of Free IgE We sought to determine whether IgE in the serum might actually provide a further beneficial effect in terms of blunting BAT activation that might be seen at high doses (60-100 µg/ml) of P6.2. Thus, we took PBMC from a donor who showed this release at higher dose P6.2 and did the BAT in the absence or presence of additional IgE. As seen in FIG. 15, activation (CD63 expression) in the presence of IgE remained at background levels compared to that without exogenous IgE, showing that free IgE may be an additional safety factor for P6.2-based therapy.

To summarize Examples 1 to 13 above, antibody P6.2 has many desirable properties as a novel therapeutic for IgE-mediated diseases (e.g., IgE-mediated allergic diseases). These properties are summarized below in Table 3.

TABLE 3

| Properties of mAb 6.2 | |
|---|---|
| Function | Status |
| Blocking cat IgE mediate BAT | Yes |
| Blocking peanut IgE mediated BAT | Yes |
| Blocking peanut IgE mediated PCA | Yes |
| Blocking cat IgE mediated PCA | Yes |
| Blocking dansyl IgE mediated PCA | Yes |
| Systemic desensitization | Yes |
| Trigger basophil activation | No |
| Trigger mast cell degranulation | No |
| Trigger systemic anaphylaxis | No |
| Surface IgE down-regulation | Yes |
| Surface Fc ∈ RI down-regulation | Yes |
| Surface IgE internalization | Yes |
| Activation of piecemeal degranulation | Yes |

At a dose of 1-2 µg/ml or 1-2 µg/gram body weight (1-2 mg/kg) range, anti-human IgE mAb P6.2 targets cell surface IgE and profoundly blocks cat (FIG. 4A), and peanut (FIG. 4B) allergic IgE-mediated basophil activation; cat, peanut and dansyl specific IgE-mediated passive cutaneous anaphylaxis (FIG. 6); and induces systemic desensitization (FIG.

Figure 13:
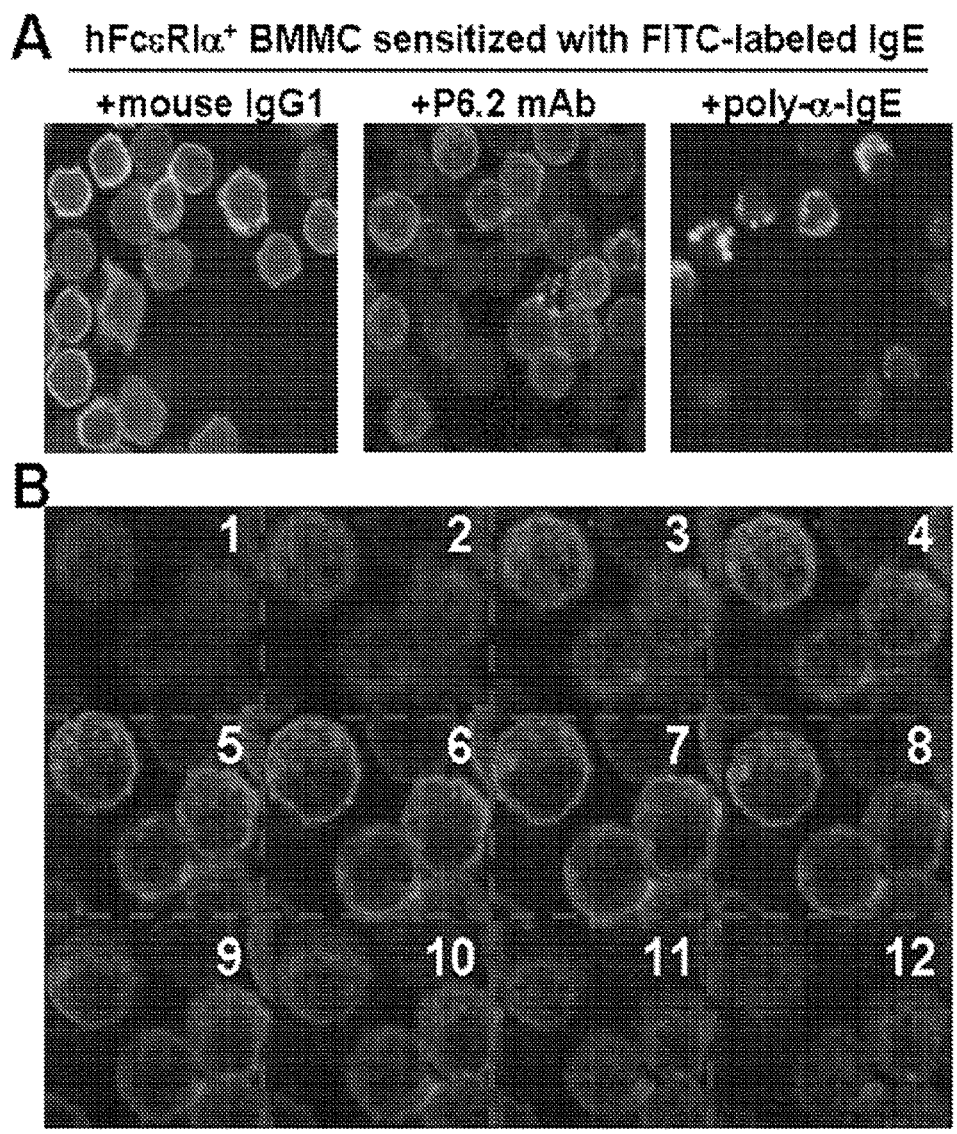
FIG. 13 provides data demonstrating that P6.2 triggers internalization of the surface bound FITC-IgE on hFcεRIα positive mast cells. A=Surface staining B=Confocal.

9). P6.2 itself at therapeutic (1-2 µg/ml) and much higher doses (30-40 µg/ml) fails to trigger the anaphylactic degranulation pathway (CD63 expression) or allergic responses in vivo (FIG. 10). Mechanistic studies reveal that P6.2 treatment down-regulates the cell surface expression of IgE and FcεRI on basophils (FIG. 11) and mast cells (FIG. 12) via driving internalization of the IgE/FcεRI complex (FIG. 13). In addition, at therapeutic doses, P6.2 triggers the basophil "piecemeal degranulation pathway" as shown by up-regulation of CD203c (FIG. 14), highlighting a potential second mechanism by which P6.2 may inhibit anaphylactic-allergic reactivity. Finally the free IgE in serum, rather than being a "sink" for P6.2 acts as a reservoir for active drug. Thus P6.2, given its low affinity, dissociates from the P6.2-IgE serum complex and functions as active drug (FIGS. 11C & FIG. 14).

Accordingly, the preceding merely illustrates the principles of the present disclosure. It will be appreciated that those skilled in the art will be able to devise various arrangements which, although not explicitly described or shown herein, embody the principles of the present disclosure and are included within its spirit and scope. Furthermore, all examples and conditional language recited herein are principally intended to aid the reader in understanding the principles of the present disclosure and the concepts contributed by the inventors to furthering the art, and are to be construed as being without limitation to such specifically recited examples and conditions. Moreover, all statements herein reciting principles, aspects, and embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

What is claimed is:

1. A method of making a pharmaceutical composition, which comprises
generating antibodies against human IgE,
selecting an antibody or fragment thereof that binds the human IgE in high affinity IgE receptors (FcεRI) on mast cells and basophils with a low affinity of $1\times10^{-5}$ M to $1\times10^{-8}$ M Kd, and
mixing the antibody or fragment thereof with a pharmaceutically acceptable carrier.

2. The method according to claim 1, wherein the antibody or fragment thereof comprises:
a heavy chain complementary determining region 1 (HCDR1) having the amino acid sequence of SEQ ID NO: 1;
a heavy chain complementary determining region 2 (HCDR2) having the amino acid sequence of SEQ ID NO: 2;
a heavy chain complementary determining region 3 (HCDR3) having the amino acid sequence of SEQ ID NO: 3;
a light chain complementary determining region 1 (LCDR1) having the amino acid sequence of SEQ ID NO: 4;
a light chain complementary determining region 2 (LCDR2) having the amino acid sequence of SEQ ID NO: 5; and
a light chain complementary determining region 3 (LCDR3) having the amino acid sequence of SEQ ID NO: 6.

3. The method according to claim 2, wherein the antibody or fragment thereof comprises a heavy chain polypeptide comprising a variable region having an amino acid sequence that is 85% or more identical to the heavy chain variable region set forth in SEQ ID NO: 7.

4. The method according to claim 2, wherein the antibody or fragment thereof comprises a light chain polypeptide comprising a variable region having an amino acid sequence that is 85% or more identical to the light chain variable region set forth in SEQ ID NO: 8.

5. The method according to claim 2, wherein the antibody or fragment thereof comprises:
a heavy chain polypeptide comprising a variable region having an amino acid sequence that is 85% or more identical to the heavy chain variable region set forth in SEQ ID NO: 7; and
a light chain polypeptide comprising a variable region having an amino acid sequence that is 85% or more identical to the light chain variable region set forth in SEQ ID NO: 8.

6. The method according to claim 1, wherein the antibody or fragment thereof is selected from the group consisting of: an IgG, Fv, scFv, Fab, F(ab')2, and Fab'.

7. The method according to claim 1, wherein the antibody or fragment thereof is a bivalent anti-IgE antibody or IgE binding fragment thereof.

8. The method according to claim 1, wherein the antibody or fragment thereof is a monoclonal anti-IgE antibody or IgE binding fragment thereof.

9. The method according to claim 1, wherein the antibody or fragment thereof is a humanized anti-IgE antibody or IgE binding fragment thereof.

10. The method according to claim 1, wherein the low affinity ranges from $1\times10^{-5}$ M to $1\times10^{-6}$ M Kd.

11. The method according to claim 1, wherein the low affinity ranges from $1\times10^{-6}$ M to $1\times10^{-7}$ M Kd.

12. The method according to claim 1, wherein the low affinity ranges from $1\times10^{-7}$ M to $1\times10^{-8}$ M Kd.

13. The method according to claim 1, wherein the concentration of the antibody or fragment thereof is about 1 mg/mL to about 200 mg/mL.

14. The method according to claim 1, wherein the concentration of the antibody or fragment thereof is about 50 mg/mL to about 200 mg/mL.

15. The method according to claim 1, wherein the concentration of the antibody or fragment thereof is about 150 mg/mL to about 200 mg/mL.

* * * * *